US008998875B2

(12) United States Patent
Lev et al.

(10) Patent No.: US 8,998,875 B2
(45) Date of Patent: Apr. 7, 2015

(54) VIAL ASSEMBLAGE WITH VIAL AND PRE-ATTACHED FLUID TRANSFER DEVICE

(75) Inventors: Nimrod Lev, Savyon (IL); Niv Ben Shalom, Netanya (IL)

(73) Assignee: Medimop Medical Projects Ltd., Ra'anana (IL)

( * ) Notice: Subject to any disclaimer, the term of this patent is extended or adjusted under 35 U.S.C. 154(b) by 603 days.

(21) Appl. No.: 13/498,378

(22) PCT Filed: Sep. 21, 2010

(86) PCT No.: PCT/IL2010/000777

§ 371 (c)(1),
(2), (4) Date: Mar. 27, 2012

(87) PCT Pub. No.: WO2011/039747

PCT Pub. Date: Apr. 7, 2011

(65) Prior Publication Data

US 2012/0184938 A1 Jul. 19, 2012

(30) Foreign Application Priority Data

Oct. 1, 2009 (IL) ........................................ 201323

(51) Int. Cl.
*A61M 5/32* (2006.01)
*B65D 51/00* (2006.01)
(Continued)

(52) U.S. Cl.
CPC ............ *B65D 51/002* (2013.01); *A61J 1/1406* (2013.01); *A61J 1/2096* (2013.01); *A61J 2001/201* (2013.01); *A61J 2001/2051* (2013.01);
(Continued)

(58) Field of Classification Search
CPC ......... A61J 1/20; A61J 1/2089; A61J 1/2096; A61J 2001/2003; A61J 2001/201; A61J 2001/2006; B65D 25/08; B65D 81/32
USPC ........................................................ 604/414
See application file for complete search history.

(56) References Cited

U.S. PATENT DOCUMENTS 62,333 A 2/1867 Holl
1,021,681 A 3/1912 Jennings (Continued)

FOREIGN PATENT DOCUMENTS

CN 1950049 A 4/2007
DE 1913926 A1 9/1970

(Continued)

OTHER PUBLICATIONS

U.S. Appl. No. 29/438,134 by Lev, filed Nov. 27, 2012.

(Continued)

*Primary Examiner* — Melanie Hand
(74) *Attorney, Agent, or Firm* — Pantich Schwarze Belisario & Nadel LLP

(57) ABSTRACT

Vial assemblages having a vial and a pre-attached fluid transfer device for use with a needleless syringe for enabling flow communication between the syringe and the vial. The fluid transfer device includes an elongated tubular flow member having a connector for sealing flow communication with the needleless syringe and a spike having a spike end for puncturing the vial for enabling flow communication between the needleless syringe and vial interior. The spike end is in intimate sealing contact with the vial's stopper. The fluid transfer device also includes a manually removable closure for initially sealing the connector and, on removal, exposing the connector.

17 Claims, 15 Drawing Sheets

(51) Int. Cl.
*A61J 1/14* (2006.01)
*A61J 1/20* (2006.01)

(52) U.S. Cl.
CPC ... *A61J2001/2055* (2013.01); *A61J 2001/2065* (2013.01); *A61J 2001/1425* (2013.01)

(56) References Cited

U.S. PATENT DOCUMENTS 1,704,817 A 3/1929 Ayers
1,930,944 A 10/1933 Schmitz, Jr.
2,326,490 A 8/1943 Perelson
2,931,668 A 4/1960 Baley
2,968,497 A 1/1961 Treleman
3,059,643 A 10/1962 Barton
D198,499 S 6/1964 Harautunelan
3,484,849 A 12/1969 Huebner et al.
3,618,637 A 11/1971 Santomieri
3,757,981 A 9/1973 Harris, Sr. et al.
3,788,524 A 1/1974 Davis et al.
3,822,700 A 7/1974 Pennington
3,826,261 A 7/1974 Killinger
3,872,992 A 3/1975 Larson
3,885,607 A 5/1975 Peltier
3,938,520 A 2/1976 Scislowicz et al.
3,957,052 A 5/1976 Topham
3,977,555 A 8/1976 Larson
3,993,063 A 11/1976 Larrabee
4,020,839 A 5/1977 Klapp
4,051,852 A 10/1977 Villari
4,109,670 A 8/1978 Slagel
4,121,585 A 10/1978 Becker, Jr.
4,161,178 A 7/1979 Genese
4,187,848 A 2/1980 Taylor
4,203,067 A 5/1980 Fitzky et al.
4,203,443 A 5/1980 Genese
4,210,173 A 7/1980 Choksi et al.
D257,286 S 10/1980 Folkman
4,253,501 A 3/1981 Ogle
4,296,786 A 10/1981 Brignola
4,303,067 A 12/1981 Connolly et al.
4,312,349 A 1/1982 Cohen
4,314,586 A 2/1982 Folkman
4,328,802 A 5/1982 Curley et al.
4,335,717 A 6/1982 Bujan et al.
D267,199 S 12/1982 Koenig
4,376,634 A 3/1983 Prior et al.
D268,871 S 5/1983 Benham et al.
4,392,850 A 7/1983 Elias et al.
4,410,321 A 10/1983 Pearson et al.
4,411,662 A 10/1983 Pearson
D271,421 S 11/1983 Fetterman
4,434,823 A 3/1984 Hudspith
4,465,471 A 8/1984 Harris et al.
4,475,915 A 10/1984 Sloane
4,493,348 A 1/1985 Lemmons
4,505,709 A 3/1985 Froning et al.
4,507,113 A 3/1985 Dunlap
D280,018 S 8/1985 Scott
4,532,969 A 8/1985 Kwaan
4,564,054 A 1/1986 Gustavsson
4,573,993 A 3/1986 Hoag et al.
4,576,211 A 3/1986 Valentini et al.
4,581,014 A 4/1986 Millerd et al.
4,588,396 A 5/1986 Stroebel et al.
4,588,403 A 5/1986 Weiss et al.
D284,603 S 7/1986 Loignon
4,604,093 A 8/1986 Brown et al.
4,607,671 A 8/1986 Aalto et al.
4,614,437 A 9/1986 Buehler
4,638,975 A 1/1987 Iuchi et al.
4,639,019 A 1/1987 Mittleman
4,667,927 A 5/1987 Oscarsson
4,676,530 A 6/1987 Nordgren et al.
4,683,975 A 8/1987 Booth et al.
4,697,622 A 10/1987 Swift et al.
4,721,133 A 1/1988 Sundblom
4,729,401 A 3/1988 Raines
4,735,608 A 4/1988 Sardam
4,743,229 A 5/1988 Chu
4,743,243 A 5/1988 Vaillancourt
4,752,292 A 6/1988 Lopez et al.
4,758,235 A 7/1988 Tu
4,759,756 A 7/1988 Forman et al.
4,778,447 A 10/1988 Velde et al.
4,787,898 A 11/1988 Raines
4,797,898 A 1/1989 Martinez
4,804,366 A 2/1989 Zdeb et al.
4,832,690 A 5/1989 Kuu
4,834,152 A 5/1989 Howson et al.
4,857,062 A 8/1989 Russell
4,865,592 A 9/1989 Rycroft
4,871,463 A 10/1989 Taylor et al.
4,898,209 A 2/1990 Zbed
4,909,290 A 3/1990 Coccia
4,931,040 A 6/1990 Haber et al.
4,932,944 A 6/1990 Jagger et al.
4,967,797 A 11/1990 Manska
D314,050 S 1/1991 Sone
D314,622 S 2/1991 Andersson et al.
4,997,430 A 3/1991 Van der Heiden et al.
5,006,114 A 4/1991 Rogers et al.
5,035,686 A 7/1991 Crittenden et al.
5,041,105 A 8/1991 D'Alo et al.
5,045,066 A 9/1991 Scheuble et al.
5,049,129 A 9/1991 Zdeb et al.
5,053,015 A 10/1991 Gross
5,061,248 A 10/1991 Sacco
5,088,996 A 2/1992 Kopfer et al.
5,096,575 A 3/1992 Cosack
5,104,387 A 4/1992 Pokorney et al.
5,113,904 A 5/1992 Aslanian
5,122,124 A 6/1992 Novacek et al.
5,125,908 A 6/1992 Cohen
5,125,915 A 6/1992 Berry et al.
D328,788 S 8/1992 Sagae et al.
5,171,230 A 12/1992 Eland et al.
5,201,705 A 4/1993 Berglund et al.
5,201,717 A 4/1993 Wyatt et al.
5,203,771 A 4/1993 Melker et al.
5,203,775 A 4/1993 Frank et al.
5,211,638 A 5/1993 Dudar et al.
5,232,029 A 8/1993 Knox et al.
5,232,109 A 8/1993 Tirrell et al.
5,242,432 A 9/1993 DeFrank
5,247,972 A 9/1993 Tetreault
D341,420 S 11/1993 Conn
5,269,768 A 12/1993 Cheung
5,270,219 A 12/1993 DeCastro et al.
5,279,576 A 1/1994 Loo et al.
5,288,290 A 2/1994 Brody
5,300,034 A 4/1994 Behnke et al.
5,301,685 A 4/1994 Guirguis
5,304,163 A 4/1994 Bonnici et al.
5,308,483 A 5/1994 Sklar et al.
5,312,377 A 5/1994 Dalton
5,328,474 A 7/1994 Raines
D349,648 S 8/1994 Tirrell et al.
5,334,163 A 8/1994 Sinnett
5,334,179 A 8/1994 Poli et al.
5,342,346 A 8/1994 Honda et al.
5,344,417 A 9/1994 Wadsworth, Jr.
5,350,372 A 9/1994 Ikeda et al.
5,364,386 A 11/1994 Fukuoka et al.
5,364,387 A 11/1994 Sweeney
5,374,264 A 12/1994 Wadsworth, Jr.
5,385,547 A 1/1995 Wong et al.
5,397,303 A 3/1995 Sancoff et al.
5,429,614 A 7/1995 Fowles et al.
5,433,330 A 7/1995 Yatsko et al.
5,445,630 A 8/1995 Richmond
5,445,631 A 8/1995 Uchida
5,451,374 A 9/1995 Molina
5,454,805 A 10/1995 Brony

(56) References Cited

U.S. PATENT DOCUMENTS

| | | | |
|---|---|---|---|
| 5,464,111 | A | 11/1995 | Vacek et al. |
| 5,464,123 | A | 11/1995 | Scarrow |
| 5,466,219 | A | 11/1995 | Lynn et al. |
| 5,466,220 | A | 11/1995 | Brenneman |
| 5,470,327 | A | 11/1995 | Helgren et al. |
| 5,471,994 | A | 12/1995 | Guirguis |
| 5,472,022 | A | 12/1995 | Michel et al. |
| 5,478,337 | A | 12/1995 | Okamoto et al. |
| 5,492,147 | A | 2/1996 | Challender et al. |
| D369,406 | S | 4/1996 | Niedospial et al. |
| 5,505,714 | A | 4/1996 | Dassa et al. |
| 5,509,433 | A | 4/1996 | Paradis |
| 5,520,659 | A | 5/1996 | Hedges |
| 5,526,853 | A | 6/1996 | McPhee et al. |
| 5,527,306 | A | 6/1996 | Haining |
| 5,531,695 | A | 7/1996 | Swisher |
| 5,547,471 | A | 8/1996 | Thompson et al. |
| 5,549,577 | A | 8/1996 | Siegel et al. |
| 5,554,128 | A | 9/1996 | Hedges |
| 5,566,729 | A | 10/1996 | Grabenkort et al. |
| 5,569,191 | A | 10/1996 | Meyer |
| 5,573,281 | A | 11/1996 | Keller |
| 5,578,015 | A | 11/1996 | Robb |
| 5,583,052 | A | 12/1996 | Portnoff et al. |
| 5,584,819 | A | 12/1996 | Kopfer |
| 5,591,143 | A | 1/1997 | Trombley, III et al. |
| 5,603,706 | A | 2/1997 | Wyatt et al. |
| 5,607,439 | A | 3/1997 | Yoon |
| 5,611,576 | A | 3/1997 | Guala |
| 5,616,203 | A | 4/1997 | Stevens |
| 5,636,660 | A | 6/1997 | Pfleiderer et al. |
| 5,637,101 | A | 6/1997 | Shillington |
| 5,641,010 | A | 6/1997 | Maier |
| 5,645,538 | A | 7/1997 | Richmond |
| 5,647,845 | A | 7/1997 | Haber et al. |
| 5,651,776 | A | 7/1997 | Appling et al. |
| 5,653,686 | A | 8/1997 | Coulter et al. |
| 5,674,195 | A | 10/1997 | Truthan |
| 5,676,346 | A | 10/1997 | Leinsing |
| 5,685,845 | A | 11/1997 | Grimard |
| 5,699,821 | A | 12/1997 | Paradis |
| 5,702,019 | A | 12/1997 | Grimard |
| 5,718,346 | A | 2/1998 | Weiler |
| D393,722 | S | 4/1998 | Fangrow, Jr. et al. |
| 5,738,144 | A | 4/1998 | Rogers |
| 5,743,312 | A | 4/1998 | Pfeifer et al. |
| 5,746,733 | A | 5/1998 | Capaccio et al. |
| 5,755,696 | A | 5/1998 | Caizza |
| 5,766,211 | A | 6/1998 | Wood et al. |
| 5,772,630 | A | 6/1998 | Ljungquist |
| 5,772,652 | A | 6/1998 | Zielinski |
| RE35,841 | E | 7/1998 | Frank et al. |
| 5,776,116 | A | 7/1998 | Lopez et al. |
| 5,782,872 | A | 7/1998 | Muller |
| 5,806,831 | A | 9/1998 | Paradis |
| 5,810,792 | A | 9/1998 | Fangrow, Jr. et al. |
| D399,559 | S | 10/1998 | Molina |
| 5,817,082 | A | 10/1998 | Niedospial, Jr. et al. |
| 5,820,621 | A | 10/1998 | Yale et al. |
| 5,827,262 | A | 10/1998 | Neftel et al. |
| 5,832,971 | A | 11/1998 | Yale et al. |
| 5,833,213 | A | 11/1998 | Ryan |
| 5,834,744 | A | 11/1998 | Risman |
| 5,839,715 | A | 11/1998 | Leinsing |
| 5,853,406 | A | 12/1998 | Masuda et al. |
| 5,871,110 | A | 2/1999 | Grimard et al. |
| 5,873,872 | A | 2/1999 | Thibault et al. |
| 5,879,337 | A | 3/1999 | Kuracina et al. |
| 5,879,345 | A | 3/1999 | Aneas |
| 5,887,633 | A | 3/1999 | Yale et al. |
| 5,890,610 | A | 4/1999 | Jansen et al. |
| 5,891,129 | A | 4/1999 | Daubert et al. |
| 5,893,397 | A | 4/1999 | Peterson et al. |
| 5,897,526 | A | 4/1999 | Vaillancourt |
| 5,899,468 | A | 5/1999 | Apps et al. |
| 5,902,280 | A | 5/1999 | Powles et al. |
| 5,902,298 | A | 5/1999 | Niedospial, Jr. et al. |
| D410,740 | S | 6/1999 | Molina |
| 5,911,710 | A | 6/1999 | Barry et al. |
| 5,919,182 | A | 7/1999 | Avallone |
| 5,921,419 | A | 7/1999 | Niedospial, Jr. et al. |
| 5,924,584 | A | 7/1999 | Hellstrom et al. |
| 5,925,029 | A | 7/1999 | Jansen et al. |
| 5,935,112 | A | 8/1999 | Stevens et al. |
| 5,941,848 | A | 8/1999 | Nishimoto et al. |
| 5,944,700 | A | 8/1999 | Nguyen et al. |
| 5,954,104 | A | 9/1999 | Daubert et al. |
| 5,971,181 | A | 10/1999 | Niedospial, Jr. et al. |
| 5,971,965 | A | 10/1999 | Mayer |
| 5,989,237 | A | 11/1999 | Fowles et al. |
| 6,003,566 | A | 12/1999 | Thibault et al. |
| 6,004,278 | A | 12/1999 | Botich et al. |
| 6,019,750 | A | 2/2000 | Fowles et al. |
| 6,022,339 | A | 2/2000 | Fowles et al. |
| 6,036,171 | A | 3/2000 | Weinheimer et al. |
| 6,039,093 | A | 3/2000 | Mrotzek et al. |
| 6,039,302 | A | 3/2000 | Cote, Sr. et al. |
| D422,357 | S | 4/2000 | Niedospial, Jr. et al. |
| 6,063,068 | A | 5/2000 | Fowles et al. |
| D427,308 | S | 6/2000 | Zinger |
| D427,309 | S | 6/2000 | Molina |
| 6,070,623 | A | 6/2000 | Aneas |
| 6,071,270 | A | 6/2000 | Fowles et al. |
| 6,080,132 | A | 6/2000 | Cole et al. |
| 6,086,762 | A | 7/2000 | Guala |
| 6,089,541 | A | 7/2000 | Weinheimer et al. |
| 6,090,091 | A | 7/2000 | Fowles et al. |
| 6,090,093 | A | 7/2000 | Thibault et al. |
| D430,291 | S | 8/2000 | Jansen et al. |
| 6,099,511 | A | 8/2000 | Devos et al. |
| 6,113,068 | A | 9/2000 | Ryan |
| 6,113,583 | A | 9/2000 | Fowles et al. |
| 6,117,114 | A | 9/2000 | Paradis |
| 6,139,534 | A | 10/2000 | Niedospial, Jr. et al. |
| 6,142,446 | A | 11/2000 | Leinsing |
| 6,146,362 | A | 11/2000 | Turnbull et al. |
| 6,149,623 | A | 11/2000 | Reynolds |
| 6,156,025 | A | 12/2000 | Niedospial, Jr. et al. |
| 6,159,192 | A | 12/2000 | Fowles et al. |
| 6,168,037 | B1 | 1/2001 | Grimard |
| 6,171,287 | B1 | 1/2001 | Lynn et al. |
| 6,171,293 | B1 | 1/2001 | Rowley et al. |
| 6,173,852 | B1 | 1/2001 | Browne |
| 6,174,304 | B1 | 1/2001 | Weston |
| 6,179,822 | B1 | 1/2001 | Niedospial, Jr. |
| 6,179,823 | B1 | 1/2001 | Niedospial, Jr. |
| 6,206,861 | B1 | 3/2001 | Mayer |
| 6,221,041 | B1 | 4/2001 | Russo |
| 6,221,054 | B1 | 4/2001 | Martin et al. |
| 6,221,065 | B1 | 4/2001 | Davis |
| 6,238,372 | B1 | 5/2001 | Zinger et al. |
| 6,245,044 | B1 | 6/2001 | Daw et al. |
| D445,501 | S | 7/2001 | Niedospial, Jr. |
| D445,895 | S | 7/2001 | Svendsen |
| 6,253,804 | B1 | 7/2001 | Safabash |
| 6,258,078 | B1 | 7/2001 | Thilly |
| 6,280,430 | B1 | 8/2001 | Neftel et al. |
| 6,290,688 | B1 | 9/2001 | Lopez et al. |
| 6,296,621 | B1 | 10/2001 | Masuda et al. |
| 6,299,131 | B1 | 10/2001 | Ryan |
| 6,343,629 | B1 | 2/2002 | Wessman et al. |
| 6,348,044 | B1 | 2/2002 | Coletti et al. |
| 6,358,236 | B1 | 3/2002 | DeFoggi et al. |
| 6,364,866 | B1 | 4/2002 | Furr et al. |
| 6,378,576 | B2 | 4/2002 | Thibault et al. |
| 6,378,714 | B1 | 4/2002 | Jansen et al. |
| 6,379,340 | B1 | 4/2002 | Zinger et al. |
| 6,382,442 | B1 | 5/2002 | Thibault et al. |
| 6,408,897 | B1 | 6/2002 | Laurent et al. |
| 6,409,708 | B1 | 6/2002 | Wessman |
| 6,440,107 | B1 | 8/2002 | Trombley, III et al. |
| 6,453,949 | B1 | 9/2002 | Chau |
| 6,453,956 | B2 | 9/2002 | Safabash |
| 6,474,375 | B2 | 11/2002 | Spero et al. |

(56) References Cited

U.S. PATENT DOCUMENTS

| | | | |
|---|---|---|---|
| 6,478,788 | B1 | 11/2002 | Aneas |
| D468,015 | S | 12/2002 | Horppu |
| 6,499,617 | B1 | 12/2002 | Niedospial, Jr. et al. |
| 6,503,240 | B1 | 1/2003 | Niedospial, Jr. et al. |
| 6,503,244 | B2 | 1/2003 | Hayman |
| 6,520,932 | B2 | 2/2003 | Taylor |
| 6,524,278 | B1 | 2/2003 | Campbell et al. |
| 6,524,295 | B2 | 2/2003 | Daubert et al. |
| D472,316 | S | 3/2003 | Douglas et al. |
| 6,530,903 | B2 | 3/2003 | Wang et al. |
| 6,537,263 | B1 | 3/2003 | Aneas |
| D472,630 | S | 4/2003 | Douglas et al. |
| 6,544,246 | B1 | 4/2003 | Niedospial, Jr. |
| 6,551,299 | B2 | 4/2003 | Miyoshi et al. |
| 6,558,365 | B2 | 5/2003 | Zinger et al. |
| 6,571,837 | B2 | 6/2003 | Jansen et al. |
| 6,572,591 | B2 | 6/2003 | Mayer |
| 6,575,955 | B2 | 6/2003 | Azzolini |
| 6,581,593 | B1 | 6/2003 | Rubin et al. |
| 6,582,415 | B1 | 6/2003 | Fowles et al. |
| 6,591,876 | B2 | 7/2003 | Safabash |
| 6,599,273 | B1 | 7/2003 | Lopez |
| 6,601,721 | B2 | 8/2003 | Jansen et al. |
| 6,626,309 | B1 | 9/2003 | Jansen et al. |
| 6,638,244 | B1 | 10/2003 | Reynolds |
| D482,121 | S | 11/2003 | Harding et al. |
| D482,447 | S | 11/2003 | Harding et al. |
| 6,651,956 | B2 | 11/2003 | Miller |
| 6,652,509 | B1 | 11/2003 | Helgren et al. |
| D483,487 | S | 12/2003 | Harding et al. |
| D483,869 | S | 12/2003 | Tran et al. |
| 6,656,433 | B2 | 12/2003 | Sasso |
| 6,666,852 | B2 | 12/2003 | Niedospial, Jr. |
| 6,681,810 | B2 | 1/2004 | Weston |
| 6,681,946 | B1 | 1/2004 | Jansen et al. |
| 6,682,509 | B2 | 1/2004 | Lopez |
| 6,692,478 | B1 | 2/2004 | Paradis |
| 6,692,829 | B2 | 2/2004 | Stubler et al. |
| 6,695,829 | B2 | 2/2004 | Hellstrom et al. |
| 6,699,229 | B2 | 3/2004 | Zinger et al. |
| 6,706,022 | B1 | 3/2004 | Leinsing et al. |
| 6,706,031 | B2 | 3/2004 | Manera |
| 6,715,520 | B2 | 4/2004 | Andreasson et al. |
| 6,729,370 | B2 | 5/2004 | Norton et al. |
| 6,736,798 | B2 | 5/2004 | Ohkubo et al. |
| 6,745,998 | B2 | 6/2004 | Doyle |
| 6,746,438 | B1 | 6/2004 | Arnissolle |
| 6,752,180 | B2 | 6/2004 | Delay |
| D495,416 | S | 8/2004 | Dimeo et al. |
| D496,457 | S | 9/2004 | Prais et al. |
| 6,802,490 | B2 | 10/2004 | Leinsing et al. |
| 6,832,994 | B2 | 12/2004 | Niedospial, Jr. et al. |
| 6,852,103 | B2 | 2/2005 | Fuller et al. |
| 6,875,203 | B1 | 4/2005 | Fowles et al. |
| 6,875,205 | B2 | 4/2005 | Leinsing |
| 6,878,131 | B2 | 4/2005 | Novacek et al. |
| 6,890,328 | B2 | 5/2005 | Fowles et al. |
| D506,256 | S | 6/2005 | Miyoshi et al. |
| 6,901,975 | B2 | 6/2005 | Aramata et al. |
| 6,945,417 | B2 | 9/2005 | Jansen et al. |
| 6,948,522 | B2 | 9/2005 | Newbrough et al. |
| 6,949,086 | B2 | 9/2005 | Ferguson et al. |
| 6,957,745 | B2 | 10/2005 | Thibault et al. |
| RE38,996 | E | 2/2006 | Crawford et al. |
| 6,994,315 | B2 | 2/2006 | Ryan et al. |
| 6,997,916 | B2 | 2/2006 | Simas, Jr. et al. |
| 6,997,917 | B2 | 2/2006 | Niedospial, Jr. et al. |
| 7,024,968 | B2 | 4/2006 | Raudabough et al. |
| 7,070,589 | B2 | 7/2006 | Lolachi et al. |
| 7,074,216 | B2 | 7/2006 | Fowles et al. |
| 7,083,600 | B2 | 8/2006 | Meloul |
| 7,086,431 | B2 | 8/2006 | D'Antonio et al. |
| 7,100,890 | B2 | 9/2006 | Cote, Sr. et al. |
| 7,140,401 | B2 | 11/2006 | Wilcox et al. |
| 7,150,735 | B2 | 12/2006 | Hickle |

| | | | |
|---|---|---|---|
| 7,192,423 | B2 | 3/2007 | Wong |
| 7,195,623 | B2 | 3/2007 | Burroughs et al. |
| 7,241,285 | B1 | 7/2007 | Dikeman |
| 7,294,122 | B2 | 11/2007 | Kubo et al. |
| 7,306,199 | B2 | 12/2007 | Leinsing et al. |
| D561,348 | S | 2/2008 | Zinger et al. |
| 7,326,188 | B1 | 2/2008 | Russell et al. |
| 7,326,194 | B2 | 2/2008 | Zinger et al. |
| 7,350,764 | B2 | 4/2008 | Raybuck |
| 7,354,422 | B2 | 4/2008 | Riesenberger et al. |
| 7,354,427 | B2 | 4/2008 | Fangrow |
| 7,425,209 | B2 | 9/2008 | Fowles et al. |
| 7,435,246 | B2 | 10/2008 | Zihlmann |
| 7,452,348 | B2 | 11/2008 | Hasegawa |
| 7,470,257 | B2 | 12/2008 | Norton et al. |
| 7,470,265 | B2 | 12/2008 | Brugger et al. |
| 7,472,932 | B2 | 1/2009 | Weber et al. |
| 7,488,297 | B2 | 2/2009 | Flaherty |
| 7,491,197 | B2 | 2/2009 | Jansen et al. |
| 7,497,848 | B2 | 3/2009 | Leinsing et al. |
| 7,523,967 | B2 | 4/2009 | Steppe |
| 7,530,546 | B2 | 5/2009 | Ryan et al. |
| D595,420 | S | 6/2009 | Suzuki et al. |
| D595,421 | S | 6/2009 | Suzuki et al. |
| 7,540,863 | B2 | 6/2009 | Haindl |
| 7,540,865 | B2 | 6/2009 | Griffin et al. |
| 7,544,191 | B2 | 6/2009 | Peluso et al. |
| D595,862 | S | 7/2009 | Suzuki et al. |
| D595,863 | S | 7/2009 | Suzuki et al. |
| 7,611,487 | B2 | 11/2009 | Woehr et al. |
| 7,611,502 | B2 | 11/2009 | Daly |
| 7,615,041 | B2 | 11/2009 | Sullivan et al. |
| 7,628,779 | B2 | 12/2009 | Aneas |
| 7,632,261 | B2 | 12/2009 | Zinger et al. |
| D608,900 | S | 1/2010 | Giraud et al. |
| 7,654,995 | B2 | 2/2010 | Warren et al. |
| 7,670,326 | B2 | 3/2010 | Shemesh |
| 7,695,445 | B2 | 4/2010 | Yuki |
| D616,090 | S | 5/2010 | Kawamura |
| 7,713,247 | B2 | 5/2010 | Lopez |
| 7,717,886 | B2 | 5/2010 | Lopez |
| 7,722,090 | B2 | 5/2010 | Burton et al. |
| D616,984 | S | 6/2010 | Gilboa |
| 7,731,678 | B2 | 6/2010 | Tennican et al. |
| 7,743,799 | B2 | 6/2010 | Mosler et al. |
| 7,744,581 | B2 | 6/2010 | Wallen et al. |
| 7,758,082 | B2 | 7/2010 | Weigel et al. |
| 7,762,524 | B2 | 7/2010 | Cawthon et al. |
| 7,766,304 | B2 | 8/2010 | Phillips |
| 7,771,383 | B2 | 8/2010 | Truitt et al. |
| 7,799,009 | B2 | 9/2010 | Niedospial, Jr. et al. |
| 7,803,140 | B2 | 9/2010 | Fangrow, Jr. |
| D627,216 | S | 11/2010 | Fulginiti |
| D630,732 | S | 1/2011 | Lev et al. |
| 7,862,537 | B2 | 1/2011 | Zinger et al. |
| 7,867,215 | B2 | 1/2011 | Akerlund et al. |
| 7,879,018 | B2 | 2/2011 | Zinger et al. |
| D634,007 | S | 3/2011 | Zinger et al. |
| 7,900,659 | B2 | 3/2011 | Whitley et al. |
| D637,713 | S | 5/2011 | Nord et al. |
| 7,985,216 | B2 | 7/2011 | Daily et al. |
| D644,104 | S | 8/2011 | Maeda et al. |
| 7,993,328 | B2 | 8/2011 | Whitley |
| 8,007,461 | B2 | 8/2011 | Huo et al. |
| 8,012,132 | B2 | 9/2011 | Lum et al. |
| 8,016,809 | B2 | 9/2011 | Zinger et al. |
| 8,021,325 | B2 | 9/2011 | Zinger et al. |
| 8,025,653 | B2 | 9/2011 | Capitaine et al. |
| 8,029,472 | B2 | 10/2011 | Leinsing et al. |
| 8,038,123 | B2 | 10/2011 | Ruschke et al. |
| 8,066,688 | B2 | 11/2011 | Zinger et al. |
| 8,070,739 | B2 | 12/2011 | Zinger et al. |
| 8,075,550 | B2 | 12/2011 | Nord et al. |
| 8,096,525 | B2 | 1/2012 | Ryan |
| 8,105,314 | B2 | 1/2012 | Fangrow, Jr. |
| D655,017 | S | 2/2012 | Mosler et al. |
| 8,122,923 | B2 | 2/2012 | Kraus et al. |
| 8,123,736 | B2 | 2/2012 | Kraushaar et al. |
| D655,071 | S | 3/2012 | Davila |

(56) References Cited

U.S. PATENT DOCUMENTS

| | | | |
|---|---|---|---|
| 8,157,784 | B2 | 4/2012 | Rogers |
| 8,167,863 | B2 | 5/2012 | Yow |
| 8,172,824 | B2 | 5/2012 | Pfeifer et al. |
| 8,177,768 | B2 | 5/2012 | Leinsing |
| 8,182,452 | B2 | 5/2012 | Mansour et al. |
| 8,187,248 | B2 | 5/2012 | Zihlmann |
| 8,196,614 | B2 | 6/2012 | Kriheli |
| 8,197,459 | B2 | 6/2012 | Jansen et al. |
| 8,211,069 | B2 | 7/2012 | Fangrow, Jr. |
| 8,225,959 | B2 | 7/2012 | Lambrecht |
| 8,241,268 | B2 | 8/2012 | Whitley |
| 8,262,628 | B2 | 9/2012 | Fangrow, Jr. |
| 8,262,641 | B2 | 9/2012 | Vedrine et al. |
| 8,267,127 | B2 | 9/2012 | Kriheli |
| D669,980 | S | 10/2012 | Lev et al. |
| 8,287,513 | B2 | 10/2012 | Ellstrom et al. |
| D673,673 | S | 1/2013 | Wang |
| D674,088 | S | 1/2013 | Lev et al. |
| D681,230 | S | 4/2013 | Mosler et al. |
| 8,454,573 | B2 | 6/2013 | Wyatt et al. |
| 8,469,939 | B2 | 6/2013 | Fangrow, Jr. |
| 8,475,404 | B2 | 7/2013 | Foshee et al. |
| 8,480,645 | B1 | 7/2013 | Choudhury et al. |
| 8,480,646 | B2 | 7/2013 | Nord et al. |
| 8,506,548 | B2 | 8/2013 | Okiyama |
| 8,511,352 | B2 | 8/2013 | Kraus et al. |
| D690,418 | S | 9/2013 | Rosenquist |
| 8,523,837 | B2 | 9/2013 | Wiggins et al. |
| 8,545,476 | B2 | 10/2013 | Ariagno et al. |
| 8,551,067 | B2 | 10/2013 | Zinger et al. |
| 8,556,879 | B2 | 10/2013 | Okiyama |
| 8,562,582 | B2 | 10/2013 | Tuckwell et al. |
| 8,608,723 | B2 | 12/2013 | Lev et al. |
| 8,628,508 | B2 | 1/2014 | Weitzel et al. |
| 8,684,992 | B2 | 4/2014 | Sullivan et al. |
| 2001/0000347 | A1 | 4/2001 | Hellstrom et al. |
| 2001/0025671 | A1 | 10/2001 | Safabash |
| 2001/0029360 | A1 | 10/2001 | Miyoshi et al. |
| 2001/0051793 | A1 | 12/2001 | Weston |
| 2002/0017328 | A1 | 2/2002 | Loo |
| 2002/0066715 | A1 | 6/2002 | Niedospial |
| 2002/0087118 | A1 | 7/2002 | Reynolds et al. |
| 2002/0087141 | A1 | 7/2002 | Zinger et al. |
| 2002/0087144 | A1 | 7/2002 | Zinger et al. |
| 2002/0121496 | A1 | 9/2002 | Thiebault et al. |
| 2002/0123736 | A1 | 9/2002 | Fowles et al. |
| 2002/0127150 | A1 | 9/2002 | Sasso |
| 2002/0128628 | A1 | 9/2002 | Fathallah |
| 2002/0138045 | A1 | 9/2002 | Moen |
| 2002/0173752 | A1 | 11/2002 | Polzin |
| 2002/0193777 | A1 | 12/2002 | Aneas |
| 2003/0028156 | A1 | 2/2003 | Juliar |
| 2003/0036725 | A1 | 2/2003 | Lavi et al. |
| 2003/0068354 | A1 | 4/2003 | Reif et al. |
| 2003/0073971 | A1 | 4/2003 | Saker |
| 2003/0100866 | A1 | 5/2003 | Reynolds |
| 2003/0109846 | A1 | 6/2003 | Zinger et al. |
| 2003/0120209 | A1 | 6/2003 | Jensen et al. |
| 2003/0153895 | A1 | 8/2003 | Leinsing |
| 2003/0187420 | A1 | 10/2003 | Akerlund et al. |
| 2003/0191445 | A1 | 10/2003 | Wallen et al. |
| 2003/0195479 | A1 | 10/2003 | Kuracina et al. |
| 2003/0199846 | A1 | 10/2003 | Fowles et al. |
| 2003/0199847 | A1 | 10/2003 | Akerlund et al. |
| 2004/0024354 | A1 | 2/2004 | Reynolds |
| 2004/0039365 | A1 | 2/2004 | Aramata et al. |
| 2004/0044327 | A1 | 3/2004 | Hasegawa |
| 2004/0073189 | A1 | 4/2004 | Wyatt et al. |
| 2004/0153047 | A1 | 8/2004 | Blank et al. |
| 2004/0181192 | A1 | 9/2004 | Cuppy |
| 2004/0204699 | A1 | 10/2004 | Hanly et al. |
| 2004/0217315 | A1 | 11/2004 | Doyle |
| 2004/0225274 | A1 | 11/2004 | Jansen et al. |
| 2004/0236305 | A1 | 11/2004 | Jansen et al. |
| 2004/0255952 | A1 | 12/2004 | Carlsen et al. |
| 2005/0015070 | A1 | 1/2005 | Delnevo et al. |
| 2005/0016626 | A1 | 1/2005 | Wilcox et al. |
| 2005/0055008 | A1 | 3/2005 | Paradis et al. |
| 2005/0082828 | A1 | 4/2005 | Wicks et al. |
| 2005/0124964 | A1 | 6/2005 | Niedospial et al. |
| 2005/0137566 | A1 | 6/2005 | Fowles et al. |
| 2005/0148994 | A1 | 7/2005 | Leinsing |
| 2005/0159724 | A1 | 7/2005 | Enerson |
| 2005/0182383 | A1 | 8/2005 | Wallen |
| 2005/0209554 | A1 | 9/2005 | Landau |
| 2005/0261637 | A1 | 11/2005 | Miller |
| 2005/0277896 | A1 | 12/2005 | Messerli et al. |
| 2006/0030832 | A1 | 2/2006 | Niedospial et al. |
| 2006/0079834 | A1 | 4/2006 | Tennican et al. |
| 2006/0089594 | A1 | 4/2006 | Landau |
| 2006/0089603 | A1 | 4/2006 | Truitt et al. |
| 2006/0095015 | A1 | 5/2006 | Hobbs et al. |
| 2006/0106360 | A1 | 5/2006 | Wong |
| 2006/0135948 | A1 | 6/2006 | Varma |
| 2006/0155257 | A1 | 7/2006 | Reynolds |
| 2006/0253084 | A1 | 11/2006 | Nordgren |
| 2007/0024995 | A1 | 2/2007 | Hayashi |
| 2007/0060904 | A1 | 3/2007 | Vedrine et al. |
| 2007/0079894 | A1 | 4/2007 | Kraus et al. |
| 2007/0083164 | A1 | 4/2007 | Barrelle et al. |
| 2007/0088252 | A1 | 4/2007 | Pestotnik et al. |
| 2007/0088293 | A1 | 4/2007 | Fangrow |
| 2007/0088313 | A1 | 4/2007 | Zinger et al. |
| 2007/0106244 | A1 | 5/2007 | Mosler et al. |
| 2007/0112324 | A1 | 5/2007 | Hamedi-Sangsari |
| 2007/0156112 | A1 | 7/2007 | Walsh |
| 2007/0167904 | A1 | 7/2007 | Zinger et al. |
| 2007/0191760 | A1 | 8/2007 | Iguchi et al. |
| 2007/0191764 | A1 | 8/2007 | Zihlmann |
| 2007/0191767 | A1 | 8/2007 | Hennessy et al. |
| 2007/0203451 | A1 | 8/2007 | Murakami et al. |
| 2007/0219483 | A1 | 9/2007 | Kitani et al. |
| 2007/0244447 | A1 | 10/2007 | Capitaine et al. |
| 2007/0244461 | A1 | 10/2007 | Fangrow |
| 2007/0244462 | A1 | 10/2007 | Fangrow |
| 2007/0244463 | A1 | 10/2007 | Warren et al. |
| 2007/0249995 | A1 | 10/2007 | Van Manen |
| 2007/0255202 | A1 | 11/2007 | Kitani et al. |
| 2007/0265574 | A1 | 11/2007 | Tennican et al. |
| 2007/0265581 | A1 | 11/2007 | Funamura et al. |
| 2007/0270778 | A9 | 11/2007 | Zinger et al. |
| 2007/0287953 | A1 | 12/2007 | Ziv et al. |
| 2007/0299404 | A1 | 12/2007 | Katoh et al. |
| 2008/0009789 | A1 | 1/2008 | Zinger et al. |
| 2008/0009822 | A1 | 1/2008 | Enerson |
| 2008/0172024 | A1 | 7/2008 | Yow |
| 2008/0249479 | A1 | 10/2008 | Zinger et al. |
| 2008/0249498 | A1 | 10/2008 | Fangrow |
| 2008/0262465 | A1 | 10/2008 | Zinger et al. |
| 2008/0287905 | A1 | 11/2008 | Hiejima et al. |
| 2008/0294100 | A1 | 11/2008 | de Costa et al. |
| 2008/0306439 | A1 | 12/2008 | Nelson et al. |
| 2008/0312634 | A1 | 12/2008 | Helmerson et al. |
| 2009/0012492 | A1 | 1/2009 | Zihlmann |
| 2009/0054834 | A1 | 2/2009 | Zinger et al. |
| 2009/0082750 | A1 | 3/2009 | Denenburg et al. |
| 2009/0143758 | A1 | 6/2009 | Okiyama |
| 2009/0177177 | A1 | 7/2009 | Zinger et al. |
| 2009/0177178 | A1 | 7/2009 | Pedersen |
| 2009/0187140 | A1 | 7/2009 | Racz |
| 2009/0216212 | A1 | 8/2009 | Fangrow, Jr. |
| 2009/0267011 | A1 | 10/2009 | Hatton et al. |
| 2009/0299325 | A1 | 12/2009 | Vedrine et al. |
| 2009/0326506 | A1 | 12/2009 | Hasegawa et al. |
| 2010/0010443 | A1 | 1/2010 | Morgan et al. |
| 2010/0022985 | A1 | 1/2010 | Sullivan et al. |
| 2010/0030181 | A1 | 2/2010 | Helle et al. |
| 2010/0036319 | A1 | 2/2010 | Drake et al. |
| 2010/0076397 | A1 | 3/2010 | Reed et al. |
| 2010/0087786 | A1 | 4/2010 | Zinger et al. |
| 2010/0137827 | A1 | 6/2010 | Warren et al. |
| 2010/0160889 | A1 | 6/2010 | Smith et al. |
| 2010/0168712 | A1 | 7/2010 | Tuckwell et al. |
| 2010/0179506 | A1 | 7/2010 | Shemesh et al. |

(56) References Cited

U.S. PATENT DOCUMENTS

| | | | |
|---|---|---|---|
| 2010/0204670 | A1 | 8/2010 | Kraushaar et al. |
| 2010/0228220 | A1 | 9/2010 | Zinger et al. |
| 2010/0241088 | A1 | 9/2010 | Ranalletta et al. |
| 2010/0274184 | A1 | 10/2010 | Chun |
| 2010/0286661 | A1 | 11/2010 | Raday et al. |
| 2010/0312220 | A1 | 12/2010 | Kalitzki |
| 2011/0004184 | A1 | 1/2011 | Proksch et al. |
| 2011/0054440 | A1 | 3/2011 | Lewis |
| 2011/0087164 | A1 | 4/2011 | Mosler et al. |
| 2011/0160701 | A1 | 6/2011 | Wyatt et al. |
| 2011/0175347 | A1 | 7/2011 | Okiyama |
| 2011/0218511 | A1 | 9/2011 | Yokoyama |
| 2011/0224640 | A1 | 9/2011 | Kuhn et al. |
| 2011/0230856 | A1 | 9/2011 | Kyle et al. |
| 2011/0264037 | A1 | 10/2011 | Foshee et al. |
| 2011/0264069 | A1 | 10/2011 | Bochenko |
| 2011/0276007 | A1 | 11/2011 | Denenburg |
| 2011/0319827 | A1 | 12/2011 | Leinsing et al. |
| 2012/0022469 | A1 | 1/2012 | Alpert |
| 2012/0053555 | A1 | 3/2012 | Ariagno et al. |
| 2012/0059346 | A1 | 3/2012 | Sheppard et al. |
| 2012/0067429 | A1 | 3/2012 | Mosler et al. |
| 2012/0078214 | A1 | 3/2012 | Finke et al. |
| 2012/0123382 | A1 | 5/2012 | Kubo |
| 2012/0215182 | A1 | 8/2012 | Mansour et al. |
| 2012/0220977 | A1 | 8/2012 | Yow |
| 2012/0220978 | A1 | 8/2012 | Lev et al. |
| 2012/0265163 | A1 | 10/2012 | Cheng et al. |
| 2012/0271229 | A1 | 10/2012 | Lev et al. |
| 2012/0296307 | A1 | 11/2012 | Holt et al. |
| 2012/0310203 | A1 | 12/2012 | Khaled et al. |
| 2012/0323187 | A1 | 12/2012 | Iwase et al. |
| 2012/0323210 | A1 | 12/2012 | Lev et al. |
| 2013/0053814 | A1 | 2/2013 | Mueller-Beckhaus et al. |
| 2013/0096493 | A1 | 4/2013 | Kubo et al. |
| 2013/0199669 | A1 | 8/2013 | Moy et al. |
| 2013/0231630 | A1 | 9/2013 | Kraus et al. |
| 2013/0237904 | A1 | 9/2013 | Deneburg et al. |
| 2013/0289530 | A1 | 10/2013 | Wyatt et al. |
| 2014/0096862 | A1 | 4/2014 | Aneas |
| 2014/0150911 | A1 | 6/2014 | Hanner et al. |

FOREIGN PATENT DOCUMENTS

| | | | |
|---|---|---|---|
| DE | 4122476 | A1 | 1/1993 |
| DE | 19504413 | A1 | 8/1996 |
| DE | 202004012714 | U1 | 11/2004 |
| DE | 202009011019 | U1 | 12/2010 |
| EP | 0192661 | A1 | 9/1986 |
| EP | 0195018 | A1 | 9/1986 |
| EP | 0258913 | A2 | 3/1988 |
| EP | 0416454 | A2 | 3/1991 |
| EP | 0518397 | A1 | 12/1992 |
| EP | 0521460 | A1 | 1/1993 |
| EP | 0637443 | A1 | 2/1995 |
| EP | 0737467 | A1 | 10/1996 |
| EP | 761562 | A1 | 3/1997 |
| EP | 765652 | A1 | 4/1997 |
| EP | 765853 | A1 | 4/1997 |
| EP | 0806597 | A1 | 11/1997 |
| EP | 0814866 | A1 | 1/1998 |
| EP | 829248 | A2 | 3/1998 |
| EP | 0856331 | A2 | 8/1998 |
| EP | 882441 | A2 | 12/1998 |
| EP | 0887085 | A2 | 12/1998 |
| EP | 0887885 | A2 | 12/1998 |
| EP | 897708 | | 2/1999 |
| EP | 0898951 | A2 | 3/1999 |
| EP | 960616 | | 12/1999 |
| EP | 1008337 | A1 | 6/2000 |
| EP | 1029526 | A1 | 8/2000 |
| EP | 1034809 | A1 | 9/2000 |
| EP | 1051988 | A2 | 11/2000 |
| EP | 1323403 | A1 | 7/2003 |
| EP | 1329210 | A1 | 7/2003 |
| EP | 1396250 | A1 | 3/2004 |
| EP | 1454609 | A1 | 9/2004 |
| EP | 1454650 | A1 | 9/2004 |
| EP | 1498097 | A2 | 1/2005 |
| EP | 1872824 | A1 | 1/2008 |
| EP | 1911432 | A1 | 4/2008 |
| EP | 1919432 | A1 | 5/2008 |
| EP | 1930038 | A2 | 6/2008 |
| EP | 2090278 | A1 | 8/2009 |
| EP | 2351548 | A1 | 8/2011 |
| EP | 2351549 | A1 | 8/2011 |
| EP | 2462913 | A1 | 6/2012 |
| FR | 2029242 | A5 | 10/1970 |
| FR | 2856660 | A1 | 12/2004 |
| FR | 2869795 | A1 | 11/2005 |
| FR | 2931363 | A1 | 11/2009 |
| GB | 1444210 | A | 7/1976 |
| IL | 171662 | | 10/2005 |
| JP | 03-062426 | B | 9/1991 |
| JP | 4329954 | A | 11/1992 |
| JP | 06-050656 | U | 7/1994 |
| JP | H08-000170 | A | 1/1996 |
| JP | 09-104460 | A | 4/1997 |
| JP | 09-104461 | A | 4/1997 |
| JP | 10-118158 | A | 5/1998 |
| JP | H10-504736 | A | 5/1998 |
| JP | 11503627 | T | 3/1999 |
| JP | 11-319031 | A | 11/1999 |
| JP | 2000-508934 | A | 7/2000 |
| JP | 2000-237278 | A | 9/2000 |
| JP | 2001-505083 | A | 4/2001 |
| JP | 2002-035140 | A | 2/2002 |
| JP | 2002-516160 | A | 6/2002 |
| JP | 2002-355318 | A | 12/2002 |
| JP | 2003-033441 | A | 2/2003 |
| JP | 2003-102807 | A | 4/2003 |
| JP | 2004-097253 | A | 4/2004 |
| JP | 2004-522541 | A | 7/2004 |
| JP | 2010-179128 | A | 8/2010 |
| WO | 9003536 | A1 | 4/1990 |
| WO | 9403373 | A1 | 2/1994 |
| WO | 9507066 | A1 | 3/1995 |
| WO | 9600053 | A1 | 1/1996 |
| WO | 9629113 | A1 | 9/1996 |
| WO | 9736636 | A1 | 10/1997 |
| WO | 9832411 | A1 | 7/1998 |
| WO | 9837854 | A1 | 9/1998 |
| WO | 9961093 | A1 | 12/1999 |
| WO | 0128490 | A1 | 4/2001 |
| WO | 0130425 | A1 | 5/2001 |
| WO | 0132524 | A1 | 5/2001 |
| WO | 0160311 | A1 | 8/2001 |
| WO | 0191693 | A2 | 12/2001 |
| WO | 0209797 | A1 | 2/2002 |
| WO | 0232372 | A1 | 4/2002 |
| WO | 0236191 | A2 | 5/2002 |
| WO | 02066100 | A2 | 8/2002 |
| WO | 02089900 | A1 | 11/2002 |
| WO | 03051423 | A2 | 6/2003 |
| WO | 03070147 | A2 | 8/2003 |
| WO | 03079956 | A1 | 10/2003 |
| WO | 2004041148 | A1 | 5/2004 |
| WO | 2005002492 | A1 | 1/2005 |
| WO | 2005041846 | A2 | 5/2005 |
| WO | 2005105014 | A2 | 11/2005 |
| WO | 2006099441 | A2 | 9/2006 |
| WO | 2007015233 | A1 | 2/2007 |
| WO | 2007017868 | A1 | 2/2007 |
| WO | 2007052252 | A1 | 5/2007 |
| WO | 2007101772 | A1 | 9/2007 |
| WO | 2007105221 | A1 | 9/2007 |
| WO | 2008081424 | A2 | 7/2008 |
| WO | 2008126090 | A1 | 10/2008 |
| WO | 2009026443 | A2 | 2/2009 |
| WO | 2009029010 | A1 | 3/2009 |
| WO | 2009038860 | A1 | 3/2009 |
| WO | 2009038860 | A2 | 3/2009 |
| WO | 2009040804 | A2 | 4/2009 |

(56) References Cited

FOREIGN PATENT DOCUMENTS

| | | | |
|---|---|---|---|
| WO | 2009087572 | A1 | 7/2009 |
| WO | 2009093249 | A1 | 7/2009 |
| WO | 2009112489 | A1 | 9/2009 |
| WO | 2009146088 | A1 | 12/2009 |
| WO | 2010061743 | A1 | 6/2010 |
| WO | 2010117580 | A1 | 10/2010 |
| WO | 2011039747 | A1 | 4/2011 |
| WO | 2011058545 | A1 | 5/2011 |
| WO | 2011058548 | A1 | 5/2011 |
| WO | 2011077434 | A1 | 6/2011 |
| WO | 2011104711 | A1 | 9/2011 |
| WO | 2012063230 | A1 | 5/2012 |
| WO | 2012143921 | A1 | 10/2012 |
| WO | 2013127813 | A1 | 9/2013 |
| WO | 2013134246 | A1 | 9/2013 |
| WO | 2013156944 | A1 | 10/2013 |
| WO | 2014033706 | A2 | 3/2014 |
| WO | 2014033710 | A1 | 3/2014 |

OTHER PUBLICATIONS

U.S. Appl. No. 29/438,141 by Gilboa, filed Nov. 27, 2012.
Written Opinion issued Aug. 16, 2012 in Int'l Application No. PCT/IL2012/000164.
English translation of an Office Action issued Sep. 10, 2013 in JP Application No. 2012-554468.
Int'l Search Report and Written Opinion issued Jan. 7, 2014 in Int'l Application No. PCT/IL2012/050721.
English translation of an Office Action issued Jan. 9, 2014 in JP Application No. 2010-526421.
English translation of an Office Action issued Dec. 4, 2013 in CN Application No. 201080051210.3.
English translation of an Office Action issued Dec. 25, 2013 in CN Application No. 201180006530.1.
Office Action issued Nov. 28, 2013 in IN Application No. 4348/DELNP/2008.
Office Action issued Oct. 8, 2013 in CN Application No. 201080043825.1.
Grifols Vial Adapter Product Literature, 2 pages, Jan. 2002.
Novel Transfer, Mixing and Drug Delivery Systems, MOP Medimop Medical Projects Ltd. Catalog, 4 pages, Rev. 4, 2004.
Smart Site.RTM. Alaris Medical Systems Product Brochure, 4 pages, Issue 1, Oct. 1999.
Smart Site.RTM. Needle-Free Systems, Alaris Medical Systems Webpage, 4 pages, Feb. 2006.
Photographs of Alaris Medical Systems SmartSite.RTM. device, 5 pages, 2002.
Non-Vented Vial Access Pin with ULTRASITE.RTM. Valve, B. Braun Medical, Inc. website and product description, 3 pages, Feb. 2006.
Office Action Issued Oct. 6, 2003 in U.S. Appl. No. 10/062,796.
Office Action Issued Feb. 22, 2005 in U.S. Appl. No. 10/062,796.
Office Action Issued Oct. 5, 2005 in U.S. Appl. No. 10/062,796.
Office Action Issued Feb. 20, 2009 in U.S. Appl. No. 11/694,297.
Int'l Search Report Issued Dec. 6, 2006 in Int'l Application No. PCT/IL2006/000912.
Int'l Preliminary Report on Patentability Issued Dec. 4, 2007 in Int'l Application No. PCT/IL2006/000912.
http://www.westpharma.com/eu/en/products/Pages/Mixject.aspx.
http://www.westpharma.com/eu/SiteCollectionDocuments/Recon/mixject%20product%20sheet.pfg: MIXJECT product information sheet pp. 1.
Int'l Search Report Issued Jul. 27, 2007 in Int'l Application No. PCT/IL2007/000343.
Int'l Preliminary Report on Patentability Issued Jun. 19, 2008 in Int'l Application No. PCT/IL2007/000343.
Int'l Search Report Issued Mar. 27, 2009 in Int'l Application No. PCT/US2008/070024.
Int'l Search Report Issued Oct. 17, 2005 in Int'l Application No. PCT/IL2005/000376.
Int'l Preliminary Report on Patentability Issued Jun. 19, 2006 in Int'l Application No. PCT/IL2005/000376.
Written Opinion of ISR Issued in Int'l Application No. PCT/IL2005/000376.
Int'l Search Report Issued Aug. 25, 2008 in Int'l Application No. PCT/IL2008/000517.
Written Opinion of the ISR Issued in Int'l Application No. PCT/IL08/00517.
Int'l Preliminary Report on Patenability Issued Oct. 20, 2009 in Int'l Application No. PCT/IL2008/000517.
Written Opinion of the Int'l Searching Authority Issued Oct. 27, 2008 in Int'l Application No. PCT/US2008/070024.
Int'l Search Report Issued Mar. 12, 2009 in Int'l Application No. PCT/IL2008/001278.
Office Action Issued in JP Application No. 2007-510229.
Office Action Issued Apr. 20, 2010 in U.S. Appl. No. 11/997,569.
Int'l Search Report dated Nov. 20, 2006 in Int'l Application No. PCT/IL2006/000881.
Office Action Issued May 27, 2010 in U.S. Appl. No. 11/559,152.
Decision to Grant mailed Apr. 12, 2010 in EP Application No. 08738307.1.
Office Action issued Jun. 1, 2010 in U.S. Appl. No. 11/568,421.
Office Action issued Nov. 12, 2010 in U.S. Appl. No. 29/334,697.
The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages.).
Publication date of Israeli Patent Application 186290 [on-line]. [Retrieved from Internet May 24, 2010]. URL:<http://www.ilpatsearch.justrice.gov.il/UI/RequestsList.aspx>. (1 page).
Int'l Search Report issued Nov. 25, 2010 in Int'l Application No. PCT/IL2010/000530.
Office Action issued Feb. 7, 2011 in U.S. Appl. No. 12/783,194.
Office Action issued Dec. 20, 2010 in U.S. Appl. No. 12/063,176.
Office Action issued Dec. 13, 2010 in U.S. Appl. No. 12/293,122.
Office Action issued Nov. 29, 2010 in U.S. Appl. No. 11/568,421.
Office Action issued Dec. 23, 2010 in U.S. Appl. No. 29/334,696.
Int'l Search Report issued on Mar. 17, 2011 in Int'l Application No. PCT/IL2010/000854.
http://www.knovel.com/web/portal/browse/display?_EXT_KNOVEL_DISPLAY_bookid=1023&VerticalID=0 [retrieved on Feb. 9, 2011].
Int'l Search Report issued on Mar. 17, 2011 in Int'l Application No. PCT/IL2010/00915.
Office Action Issued May 12, 2011 in U.S. Appl. No. 12/063,176.
Office Action issued Jul. 11, 2011 in U.S. Appl. No. 12/293,122.
Int'l Search Report issued Jul. 12, 2011 in Int'l Application No. PCT/IL2011/000187.
Int'l Search Report issued Jul. 12, 2011 in Int'l Application No. PCT/IL2011/000186.
Office Action issued Aug. 3, 2011 in JP Application No. 2008-525719.
Int'l Search Report issued Oct. 7, 2011 in Int'l Application No. PCT/IL2011/000511.
Int'l Search Report issued Mar. 6, 2012 in Int'l Application No. PCT/IL2011/000834; Written Opinion.
U.S. Appl. No. 13/522,410 by Lev, filed Jul. 16, 2012.
U.S. Appl. No. 13/576,461 by Lev, filed Aug. 1, 2012.
Office Action issued Jun. 14, 2012 in U.S. Appl. No. 29/376,980.
Office Action issued Jun. 15, 2012 in U.S. Appl. No. 29/413,170.
Office Action issued Jun. 21, 2012 in U.S. Appl. No. 12/596,167.
Written Opinion issued Jul. 1, 2013 in Int'l Application No. PCT/IL2013/050180.
Int'l Preliminary Report on Patentability issued Apr. 1, 2014 in Int'l Application No. PCT/IL2013/050180.
Written Opinion issued Jul. 31, 2013 in Int'l Application No. PCT/IL2013/050313.
Int'l Preliminary Report on Patentability issued May 12, 2014 in Int'l Application No. PCT/IL2013/050316.
Office Action issued Jul. 31, 2014 in U.S. Appl. No. 29/438,141 by Gilboa.
U.S. Appl. No. 14/385,212 by Lev, filed Sep. 15, 2014.
U.S. Appl. No. 29/502,037 by Lev, filed Sep. 11, 2014.

(56) References Cited

OTHER PUBLICATIONS

U.S. Appl. No. 29/502,053 by Lev, filed Sep. 11, 2014.
U.S. Appl. No. 14/391,792 by Lev, filed Oct. 10, 2014.
U.S. Appl. No. 14/504,979 by Lev, filed Oct. 2, 2014.
Int'l Search Report and Written Opinion issued Sep. 2, 2014 in Int'l Application No. PCT/IL2014/050405.
Int'l Search Report and Written Opinion issued Oct. 17, 2014 in Int'l Application No. PCT/IL2014/050680.
English translation of an Office Action issued Aug. 28, 2014 in JP Application No. 2013-168885.
Int'l Preliminary Report on Patentability issued Sep. 24, 2013 in Int'l Application No. PCT/IL2012/000354.
Office Action issued Feb. 13, 2014 in U.S. Appl. No. 13/884,981 by Denenburg.
U.S. Appl. No. 14/345,094 by Lev, filed Mar. 14, 2014.
Int'l Search Report issued Jan. 22, 2013 in Int'l Application No. PCT/IL2012/000354.
Int'l Search Report issued Mar. 18, 2013 in Int'l Application No. PCT/IL2012/050516.
Office Action issued Apr. 2, 2013 in U.S. Appl. No. 13/505,790.
Int'l Search Report and Written Opinion issued Mar. 6, 2012 in Int'l Application No. PCT/IL2011/000834.
U.S. Appl. No. 13/883,289 by Lev, filed May 3, 2013.
Office Action issued Mar. 1, 2012 in JP Application No. 2007-510229.
Int'l Search Report issued Mar. 7, 2012 in Int'l Application No. PCT/IL2011/000829; Written Opinion.
Office Action issued Mar. 13, 2012 in CA Application No. 2,563,643.
Office Action issued Mar. 1, 2012 in CN Application No. 200880108283.4.
Office Action issued Mar. 6, 2012 in U.S. Appl. No. 12/678,928.
Int'l Search Report issued Feb. 3, 2011 in Int'l Application No. PCT/IL2010/000777; Written Opinion.
Int'l Search Report issued Mar. 17, 2011 in Int'l Application No. PCT/IL2010/000854; Written Opinion.
Int'l Search Report issued Mar. 17, 2011 in Int'l Application No. PCT/IL2010/000915; Written Opinion.
U.S. Appl. No. 13/505,790 by Lev, filed May 3, 2012.
U.S. Appl. No. 13/505,881 by Lev, filed May 3, 2012.
Int'l Search Report & Written Opinion issued on Mar. 7, 2012 in Int'l Application No. PCT/IL2011/000829.
U.S. Appl. No. 13/884,981 by Denenburg, filed May 13, 2013.
Office Action issued May 31, 2013 in U.S. Appl. No. 13/505,790.
English translation of an Office Action issued Feb. 4, 2014 in JP Application No. 2012-554468.
Office Action issued Jan. 17, 2014 in CN Application No. 201180006534.X.
Int'l Search Report and Written Opinion issued May 8, 2014 in Int'l Application No. PCT/IL2013/050706.
English translation of an Office Action issued Apr. 28, 2014 in JP Application No. 2013-537257.
Int'l Preliminary Report on Patentability issued Jan. 14, 2014 in Int'l Application No. PCT/IL2012/050516.
Office Action issued May 6, 2014 in U.S. Appl. No. 13/505,881 by Lev.
U.S. Appl. No. 14/366,306 by Lev, filed Jun. 18, 2014.
Office Action issued Apr. 17, 2014 in CN Application No. 201080051201.4.
Int'l Search Report issued Jun. 5, 2013 in Int'l Application No. PCT/IL2012/050407.
Int'l Search Report issued Jun. 19, 2013 in Int'l Application No. PCT/IL201/050167.
Int'l Search Report issued Jul. 1, 2013 in Int'l Application No. PCT/IL2013/050180.
Int'l Search Report issued Jul. 31, 2103 in Int'l Application No. PCT/IL2013/050313.
Int'l Search Report issued Jul. 26, 2013 in Int'l Application No. PCT/IL2013/050316.
English translation of an Office Action issued Jun. 19, 2013 in JP Application No. 2012-531551.
Office Action issued Aug. 20, 2013 in U.S. Appl. No. 13/576,461 by Lev.
Int'l Search Report issued Jun. 19, 2013 in Int'l Application No. PCT/IL2013/050167.
Int'l Preliminary Report on Patentability issued Aug. 28, 2012 in Int'l Application No. PCT/IL2011/000186.
U.S. Appl. No. 14/005,751 by Denenburg, filed Sep. 17, 2013.
English translation of an Office Action issued Jul. 26, 2013 in JP Application No. 2012-538464.
International Search Report Issued Jan. 23, 2007 in Int'l Application No. PCT/IL/2006/001228.
IV disposables sets catalogue, Cardinal Health, Alaris® products, SmartSite® access devices and accessories product No. 10013365, SmartSite add-on bag access device with spike adapter and needle-free valve bag access port, pp. 1-5, Fall edition (2007).
Drug Adminsitration Systems product information sheets; http://www.westpharma.com/eu/en/products/Pages/Vial2Bag.aspx; pp. 1-3 (admitted prior art).
Office Action Issued Jun. 8, 2010 in U.S. Appl. No. 12/112,490 by Zinger.
Office Action issued Sep. 28, 2010 in U.S. Appl. No. 12/112,490 by Zinger.
Article with picture of West Pharmaceutical Services' Vial2Bag Needleless System, [on-line]; ISIPS Newsletter, Oct. 26, 2007]; retrieved from Internet Feb. 16, 2010]; URL:<http://www.isips.org/reports/ISIPS_Newsletter_October_26_2007.html.> (7 pages. see pp. 5-6).
Office Action issued Jun. 15, 2011 in JP Application No. 2008-538492.
Translation of Office Action issued Jun. 18, 2012 in JP Application No. 2008-538492.
Translation of Office Action issued Apr. 15, 2013 in JP Application No. 2008-538492.
Office Action issued Jul. 13, 2012 in U.S. Appl. No. 12/112,490 by Zinger.
Office Action issued Jan. 23, 2013 in U.S. Appl. No. 12/112,490 by Zinger.
Int'l Preliminary Report on Patentability issued May 6, 2008 in Int'l Application No. PCT/IL2006/001228.
Int'l Search Report issued Aug. 16, 2012 in Int'l Application No. PCT/IL2012/000164.
Int'l Search Report and Written Opinion issued Jul. 16, 2014 in Int'l Application No. PCT/IL2014/050327.
English translation of an Office Action issued Jun. 30, 2014 in CN Application No. 201180052962.6.
Extended European Search Report issued Jun. 3, 2014 in EP Application No. 08781828.2.
Office Action issued Nov. 11, 2013 in IL Application No. 218730.
U.S. Appl. No. 29/478,723 by Lev, filed Jan. 8, 2014.
U.S. Appl. No. 29/478,726 by Lev, filed Jan. 8, 2014.
Office Action issued Jan. 2, 2014 in U.S. Appl. No. 13/505,881 by Lev.

VIAL ASSEMBLAGE WITH VIAL AND PRE-ATTACHED FLUID TRANSFER DEVICE

CROSS-REFERENCE TO RELATED APPLICATION

This application is a Section 371 of International Application No. PCT/IL2010/000777, filed Sep. 21, 2010, which was published in the English language on Apr. 7, 2011, under International Publication No. WO 2011/039747 A1, and the disclosure of which is incorporated herein by reference.

FIELD OF THE INVENTION

This invention relates to vial assemblages including a vial with a pre-attached fluid transfer device for use with a needleless syringe.

BACKGROUND OF THE INVENTION

Liquid drug reconstitution for reconstitution of medicaments supplied in vials generally involves multiple steps including inter alia opening a vial adapter package for preparing a vial adapter with a cannula for use, preparing a sealed vial for use, co-axial alignment of the vial adapter with the vial and subsequent manually snap fitting the vial adapter onto the vial such that the vial adapter's cannula punctures the vial's stopper. Such vial adapters are commercially available from, for example, Medimop Medical Projects Ltd, Ra'anana, Israel. Such multiple steps take considerable preparation time and introduce a margin for error in the procedure. Moreover, many users inadvertently misalign the vial adapter with the vial such that the former's cannula is unable to puncture the vial's stopper for flow communication purposes. Furthermore, some users initially accurately align the vial adapter with the vial but then incline the vial adapter while manually snap fitting the same for puncturing the vial, thereby precluding flow communication.

Vial assemblages with a vial and a pre-attached fluid transfer device are illustrated and described in inter alia EP 1 008 337, EP 1 029 526, FR 2 029 242, GB 1 442 210, U.S. Pat. Nos. 2,326,490, 6,090,093, 6,681,946, US 2002/121496, WO 94/03373, WO 96/00053, WO 98/32411, WO 98/37854, WO 01/28490, WO 01/32524 and WO 2007/015233.

SUMMARY OF THE INVENTION

The present invention is directed towards vial assemblages with a vial and a pre-attached fluid transfer device for use with a needleless syringe for enabling flow communication between the syringe and the vial. Vials are typically sealed by a stopper in a conventional manner. Stoppers have a preformed axial blind bore with a bore end leaving a reduced stopper thickness between the bore end and the vial interior. Fluid transfer devices have an elongated tubular flow member including a connector and a spike for initial intimate sealing non-puncturing pre-insertion into the blind bore. Connectors are sealed by a closure for maintaining sterile conditions. Spike tips are in proximity to or possibly contacting a bore end for facilitating stopper puncturing for establishing flow communication with vial interiors. Connectors preferably have an external screw thread and closures are preferably constituted by a screw cap screw threaded thereon. Connectors can be either female or male for suitable sealing flow communication with a syringe with a mating connector. Connectors are preferably Luer connectors. Other suitable closures include inter alia a tear off seal, and the like.

Fluid transfers device are manually urged from an initial non-communication set-up position to a flow communication position. Fluid transfer devices preferably include a flow member arrest arrangement for stopping displacement of a flow member towards a vial on manual urging to its flow communication position such that its spike end protrudes a predetermined distance into a vial interior for flow communication purposes. Fluid transfer devices also preferably include a flow member securing arrangement for preventing manual removal of a closure inadvertently withdrawing a flow member from its blind bore. In the case of a screw cap, flow member securing arrangements prevent rotation of the flow member relative to the stopper during unscrewing of the screw cap and screwing a syringe onto the connector.

Fluid transfer devices may also include a safety catch mechanism requiring priming for subsequent manual depression of a fluid transfer device from a non-flow communication set-up position to a flow communication position for precluding inadvertent stopper puncturing. Safety catch mechanisms preferably lock a flow member so that its movement is substantially prevented towards or away from a vial until released. Safety catch mechanisms may also include a tamper-proof arrangement which prevents a user returning a safety catch mechanism to its initial position once a user has primed same ready for manually urging its flow member from an initial non-flow communication set-up position to a subsequent flow communication position.

Vial assemblages of the present invention afford convenient and sterile liquid drug reconstitution precluding the initial preparation steps of a vial and a vial adapter and the subsequent assembly steps of aligning a vial adapter with a vial before snap fitting the former on the latter. Moreover, by virtue of the stoppers having a considerably reduced thickness at their bore ends compared to conventional stoppers, the pre-inserted spikes are ensured to puncture through the stoppers to achieve flow communication with the vial interiors. Furthermore, the blind bores act to guide their pre-inserted spikes during aforesaid manual depression thereby reducing the likelihood of inadvertent inclination of a fluid transfer device with respect to a vial.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE INVENTION

Figure 1:
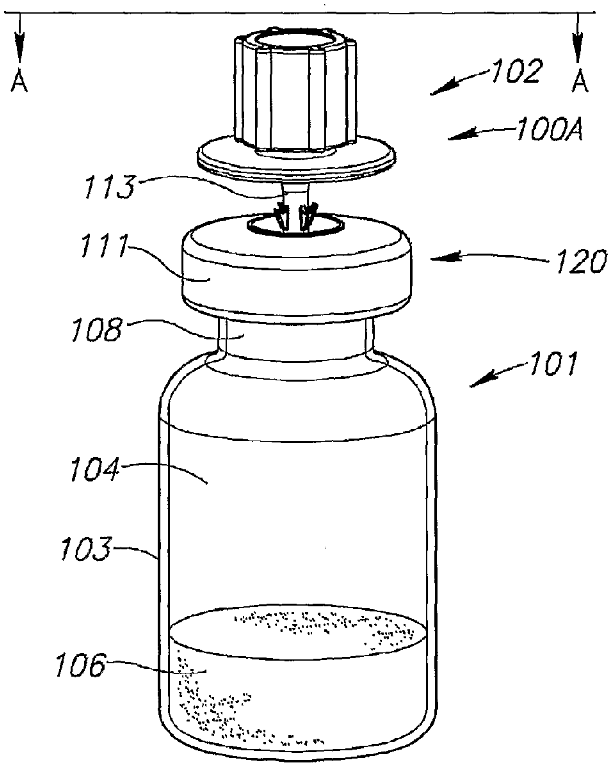
FIG. 1 is a front isometric view of an upright vial assemblage including a vial and a first preferred embodiment of a pre-attached fluid transfer device in an initial non-flow communication set-up position.
Figure 2:
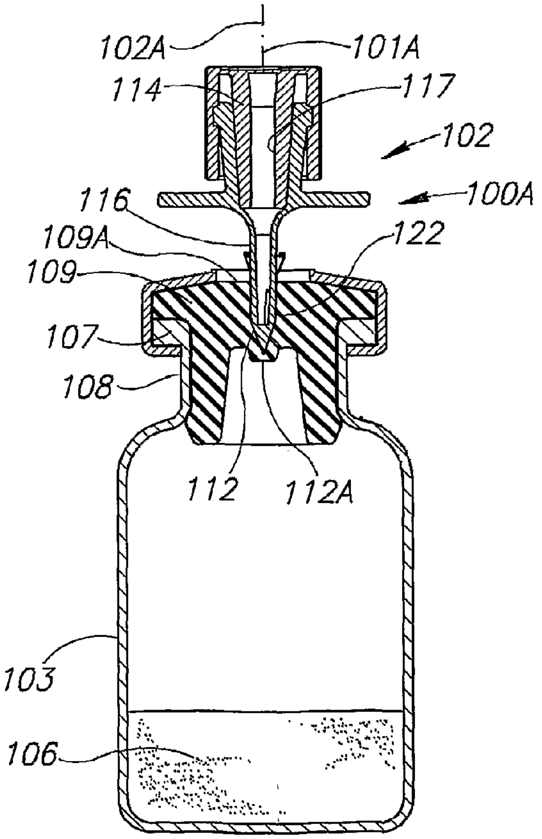
FIG. 2 is a longitudinal cross section\n of FIG. 1's vial assemblage along line A-A in FIG. 1.
Figure 3:
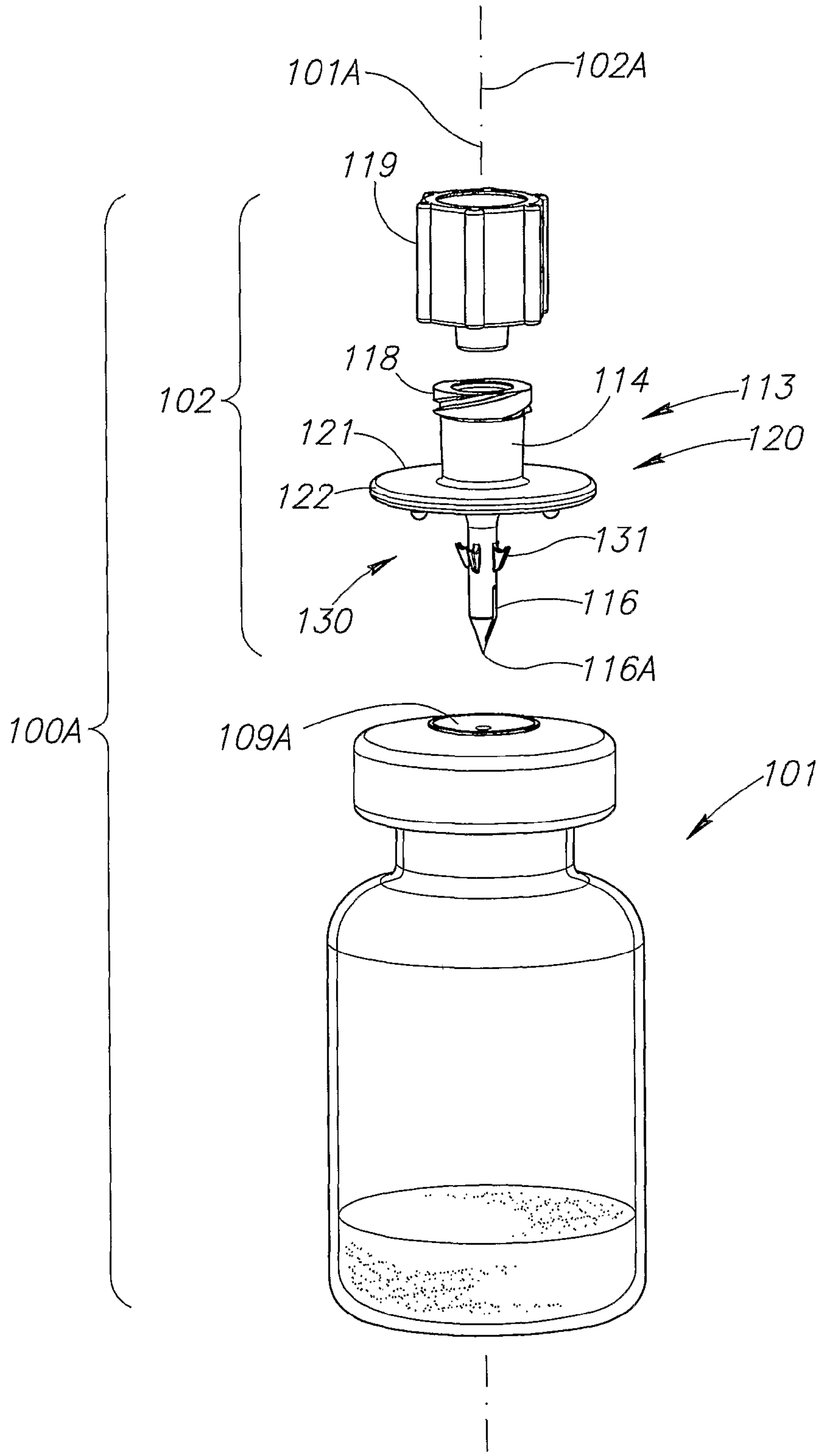
FIG. 3 is an exploded view of FIG. 1's vial assemblage.

FIGS. 1 to 5 show a vial assemblage 100A having a two part construction including a vial 101 and a pre-attached fluid transfer device 102. The vial 101 has a longitudinal axis 101A and includes a vial body 103 having a vial interior 104 for storing a powdered or liquid medicament 106, a vial rim 107 defining a vial opening, and an intermediate narrow diameter vial neck 108 between the vial interior 104 and the vial rim 107. The vial 101 is sealed by a stopper 109 having an exposed uppermost stopper surface 109A. The vial 101 is hermetically sealed by a band 111. The stopper 109 is formed with a blind bore 112 with a bore end 112A of reduced stopper thickness between the bore end 112A and the vial interior 104.

The fluid transfer device 102 has a longitudinal axis 102A substantially co-axial with the longitudinal axis 101A and includes an elongated tubular flow member 113. The flow member 113 includes a connector 114, a spike 116, and a single lumen 117 extending lengthwise between the connector 114 and the spike 116 for flow communication therebetween. The spike 116 is in intimate sealing contact with the stopper 109 and has a spike end 116A proximate the bore end 112A not puncturing the stopper 109 in an initial non-flow communication set-up position (see FIGS. 1 and 2) and puncturing through the bore end 112A in a flow communication position (see FIGS. 4 and 5). The connector 114 has an external screw thread 118 sealed by a closure 119 constituted by a screw cap for keeping the connector 114 sterile. The connector 114 shown in the drawings is a female Luer connector.

Figure 4:
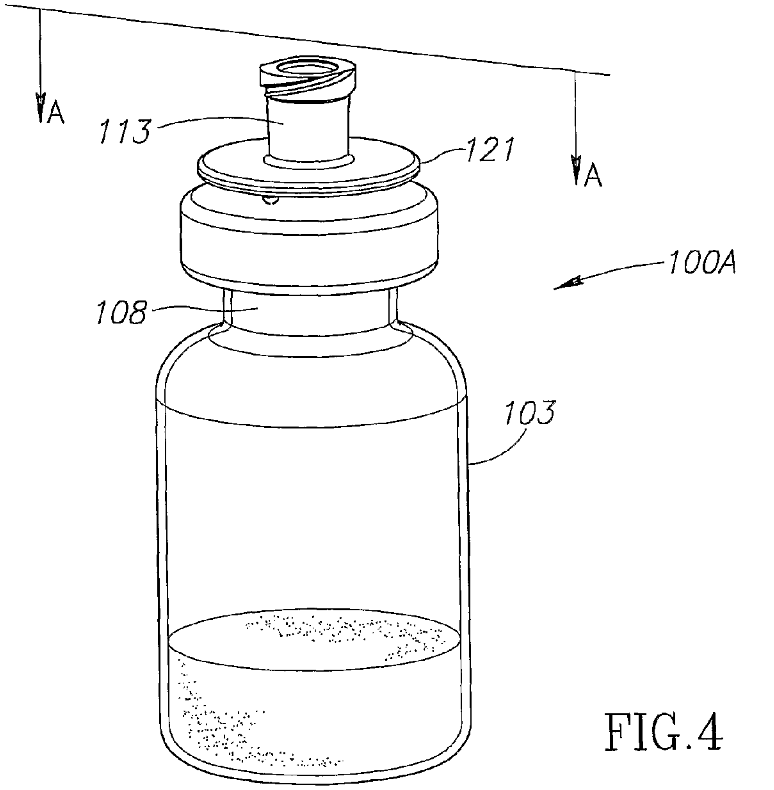
FIG. 4 is a front isometric view of FIG. 1's vial assemblage in a subsequent flow communication position.
Figure 5:
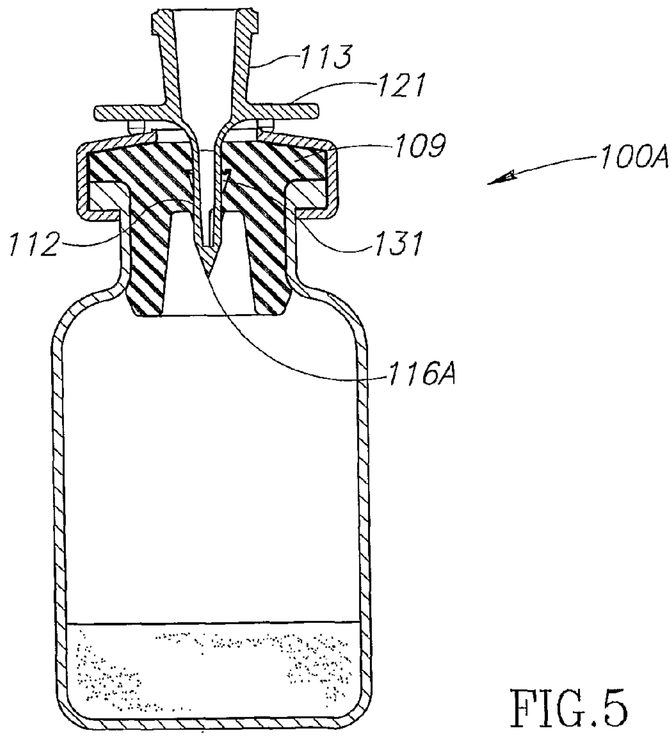
FIG. 5 is a longitudinal cross section of FIG. 4's vial assemblage along line A-A in FIG. 4.

The fluid transfer device 102 includes a flow member arrest arrangement 120 for stopping displacement of the flow member 113 toward the vial 101 such that the spike end 116A punctures through the stopper 109 to a predetermined distance for flow communication purposes on manual urging of the flow member 113 from its non-flow communication set-up position (see FIGS. 1 and 2) to its flow communication position (see FIGS. 4 and 5). The flow member arrest arrangement 120 is constituted by an annular flange 121 intermediate the connector 114 and the spike 116 disposed above the uppermost stopper surface 109A in the non-flow communication set-up position and bearing thereagainst in the flow communication position.

The fluid transfer device 102 includes a flow member securing arrangement 130 for displacement of the flow member 113 from the stopper 109 on manual removal of the closure 119 from the connector 114. The flow member securing arrangement 130 prevents rotation of the flow member 113 relative to the stopper 109 during unscrewing of the screw cap 119 and subsequent screwing a syringe 140 onto the connector 114. The flow member securing arrangement 130 is constituted by a pair of opposite radial barbs 131 disposed above the stopper surface 109A in the vial assemblage 100A's set-up position (see FIGS. 1 and 2) and inserted into the stopper 109 in the vial assemblage 100A's flow communication position (see FIGS. 4 and 5).

Figure 7:
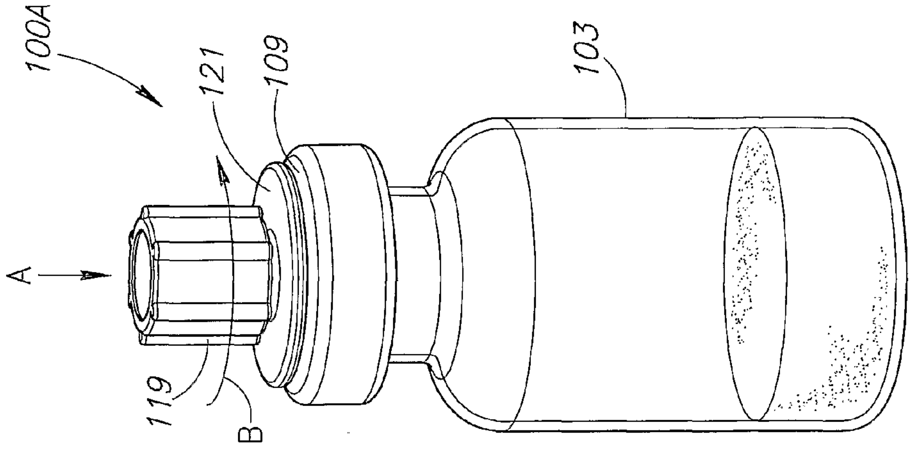
FIGS. 6 to 8 show the use of FIG. 1's vial assemblage.
Figure 6:
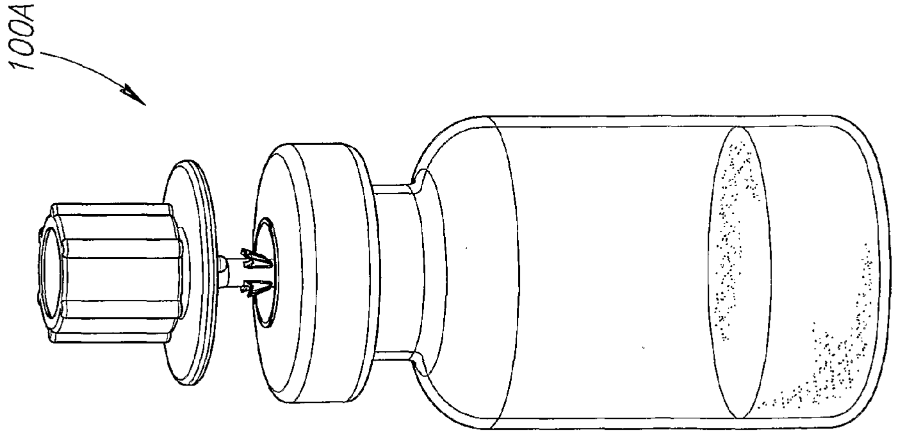
Figure 8:
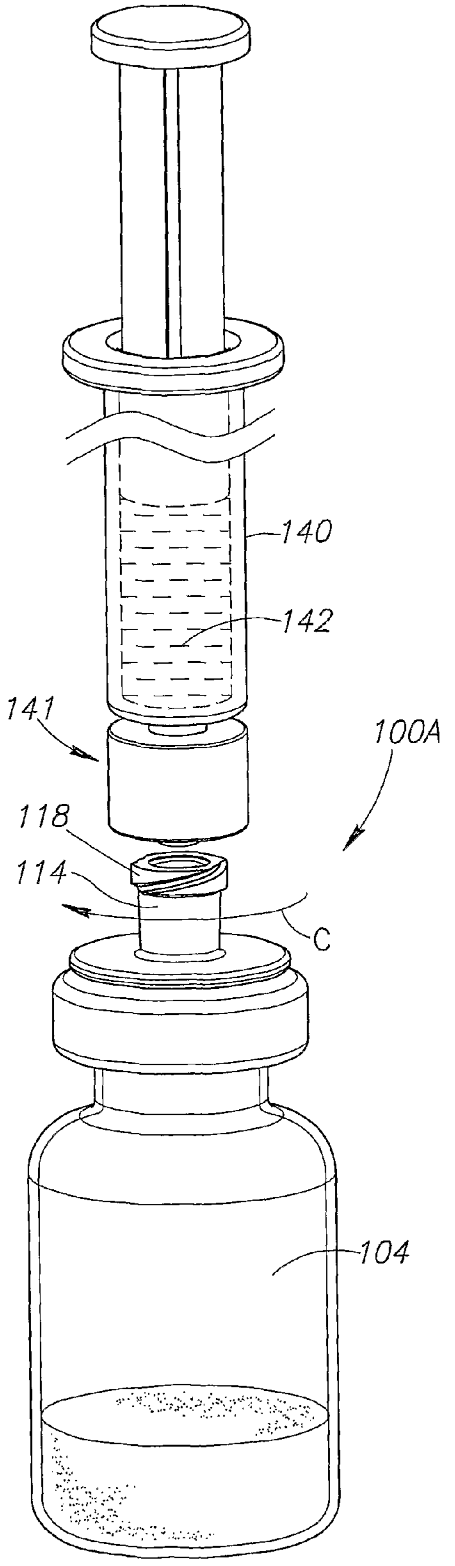

FIGS. 6 to 8 show the use of the vial assemblage 100A with a syringe 140 having a male Luer lock connector 141 and containing a diluent 142 for reconstituting the vial's powder medicament 106 as follows:

FIG. 6 shows the vial assemblage 100A in its set-up position in which the spike 116 does not puncture the stopper 109 and the screw cap 119 seals the connector 114.

FIG. 7 shows the vial assemblage 100A in its flow communication position after depression of the flow member 113 towards the vial 101 as depicted by arrow A until it is stopped by the flange 121 bearing against the stopper surface 109A and the spike end 116A has punctured the stopper 109.

FIG. 8 shows the vial assemblage 100A after unscrewing the screw cap 119 in a counterclockwise direction B to expose the connector 114. The barbs 131 prevent rotation of the flow member 113 while unscrewing the screw cap 119 and also withdrawal of the flow member 113 from the stopper 109.

The syringe 140 is screwed in a clockwise direction C onto the connector 114 for enabling flow communication between the syringe 140 and the vial interior 104. The barbs 131 prevent rotation of the flow member 113 while screwing the syringe 140 onto the connector 114.

Figure 9:
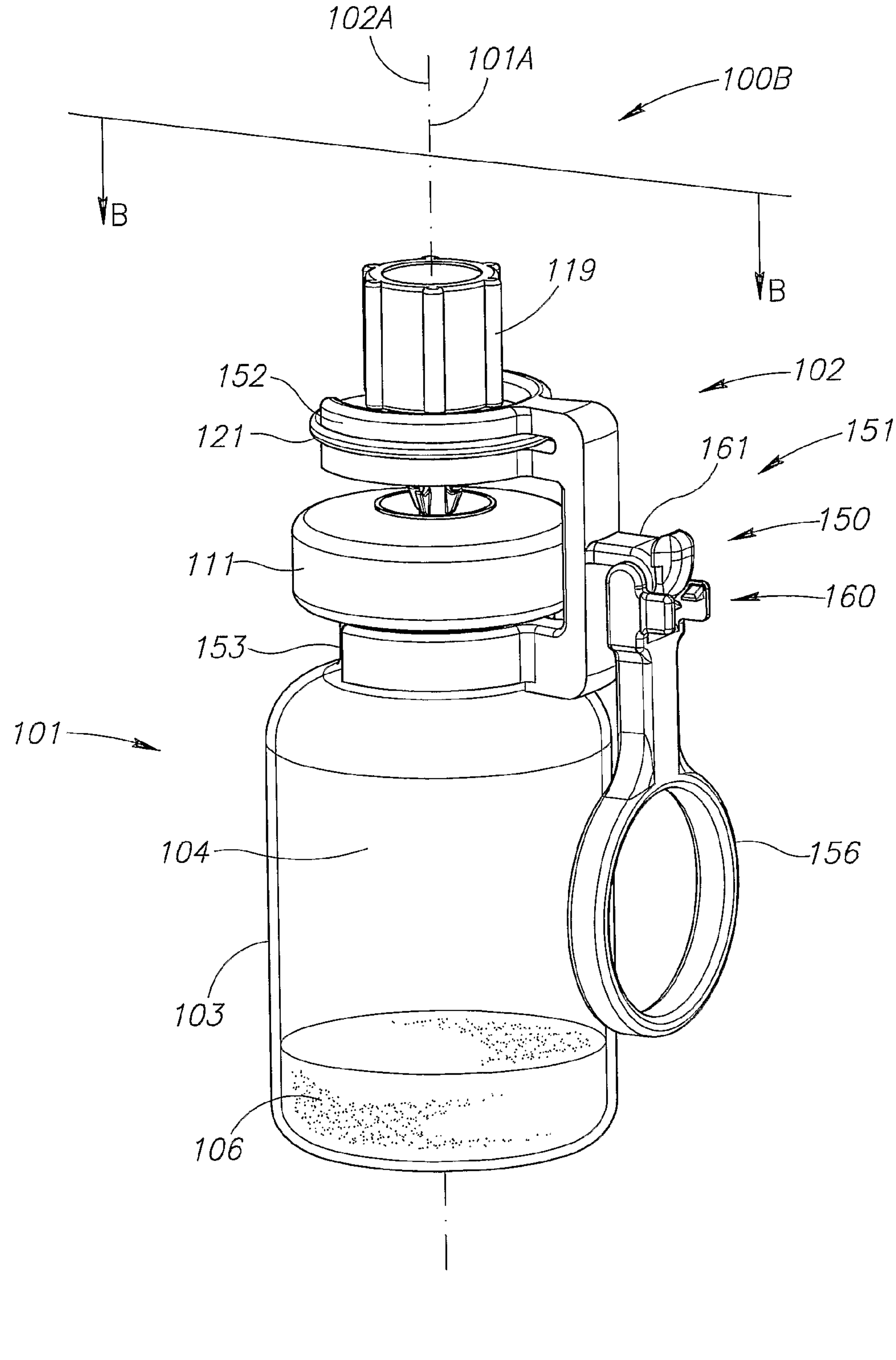
FIG. 9 is a front isometric view of an upright vial assemblage including a vial and a second preferred embodiment of a pre-attached fluid transfer device having a pull ring type safety catch mechanism in an initial set-up position.
Figure 10:
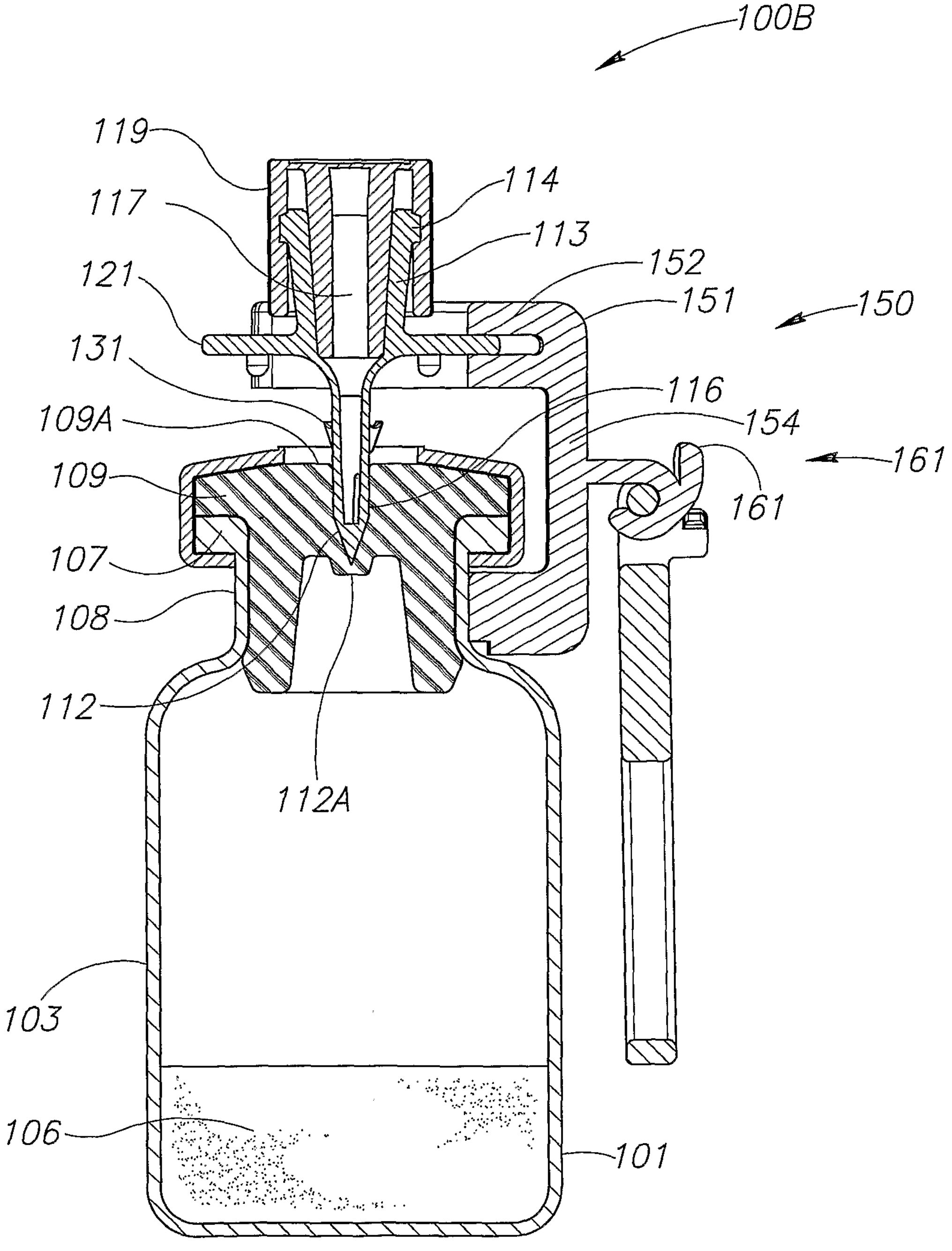
FIG. 10 is a longitudinal cross section of FIG. 9's vial assemblage along line B-B in FIG. 9.
Figure 11:
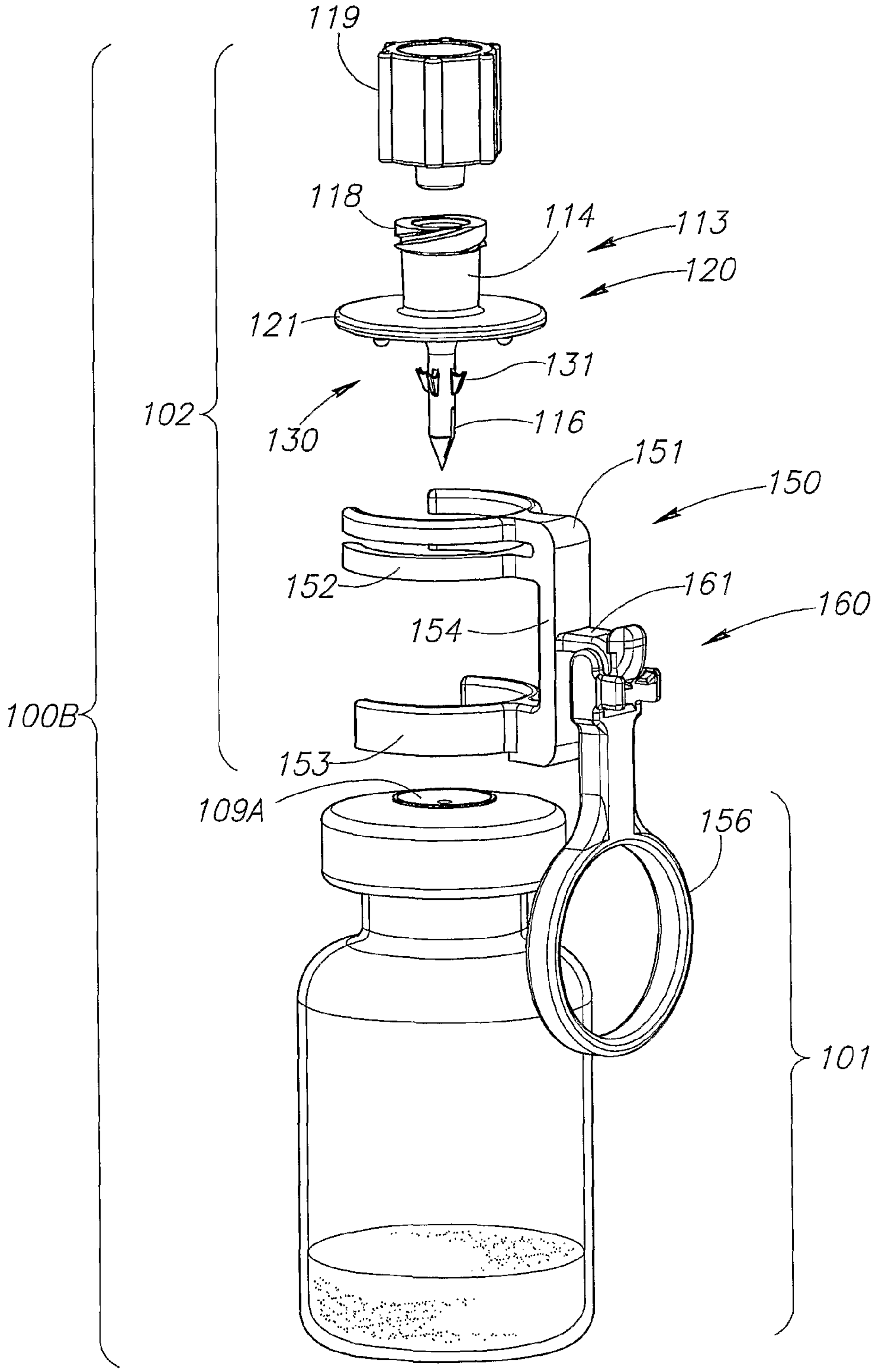
FIG. 11 is an exploded view of FIG. 9's vial assemblage.

FIGS. 9 to 11 show a vial assemblage 100B similar to the vial assemblage 100A and therefore similar parts are likewise numbered. The vial assemblage 100B differs from the vial assemblage 100A insofar the former includes a fluid transfer device 102 with a pull ring type safety catch mechanism 150 for preventing inadvertent displacement of the flow member 113 from its set-up position towards its flow communication position leading to an inadvertent puncturing of the stopper 109.

The safety catch mechanism 150 includes a safety catch 151 having an upper near annular split flange grip 152 for gripping the flange 122, a lower near annular neck grip 153 for gripping the vial neck 108, and an upright rod 154 extending between the flange grip 152 and the neck grip 153. The safety catch mechanism 150 also includes a safety pull ring 156 for removing the safety catch 151 thereby allowing the flow member 113 to be manually depressed towards the vial 101. The safety pull ring 156 has an initial downward position co-directional with the vial's longitudinal axis 101A and is manually urged upwards into a subsequent transverse position relative to the vial's longitudinal axis 101A for enabling removal of the safety catch 151.

The safety catch mechanism 150 includes a tamper-proof arrangement 160 for preventing a user returning the safety catch mechanism 150 to its initial position once a user has primed same ready for manually urging the flow member 113 from its initial set-up position to its subsequent flow communication position. The tamper-proof arrangement 160 is constituted by the upright rod 154 being formed with a detent 161 for precluding the safety ring 156 to return from its subsequent transverse position to its initial downward position, thereby ensuring that the vial assemblage 100B is tamper proof.

Figure 13:
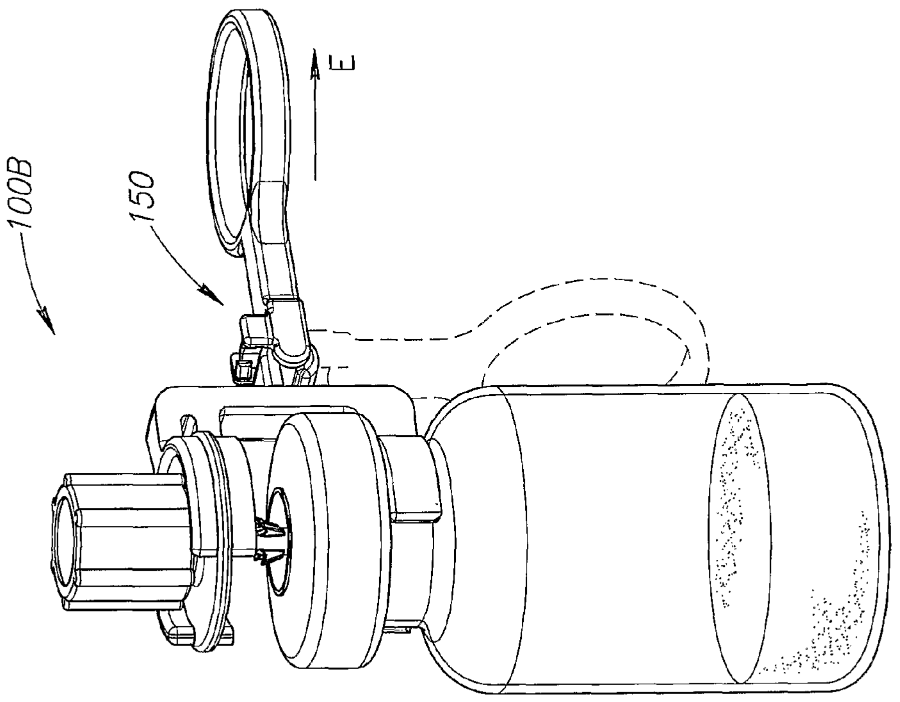
FIGS. 12 and 13 show removal of the safety catch mechanism.
Figure 12:
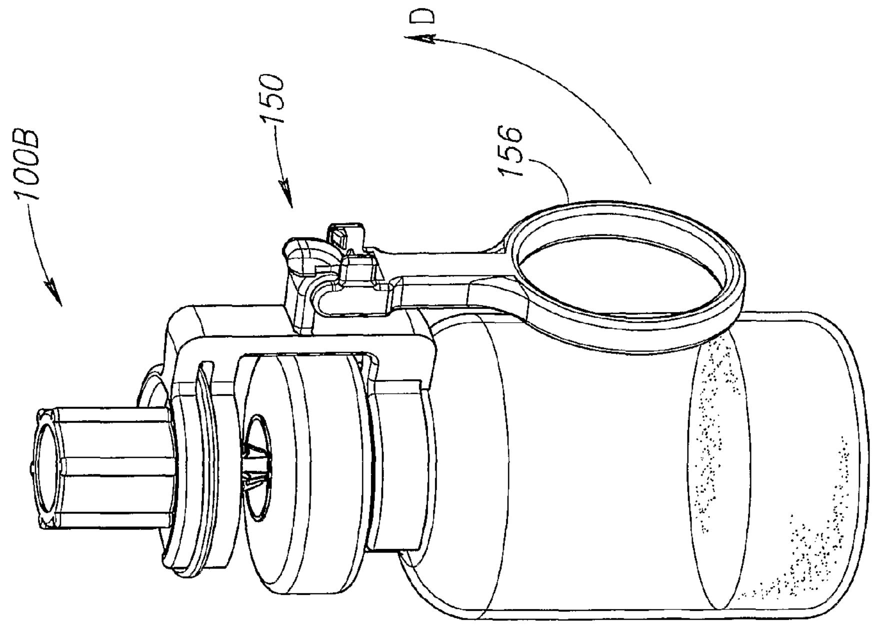

The use of the vial assemblage 100B is similar to the vial assemblage 100A except in this case the safety catch mechanism 150 has to be initially primed and then removed before operation as per the steps shown in FIGS. 6 to 8. FIG. 12 shows initial priming of the vial assemblage 100B by manually urging the safety ring 156 upward from its initial downward position as depicted by arrow D to its transverse position shown in solid lines in FIG. 13. FIG. 13 shows final priming of the vial assemblage 100B ready for use following sideways removal of the safety catch mechanism 150 as depicted by arrow E.

Figure 15:
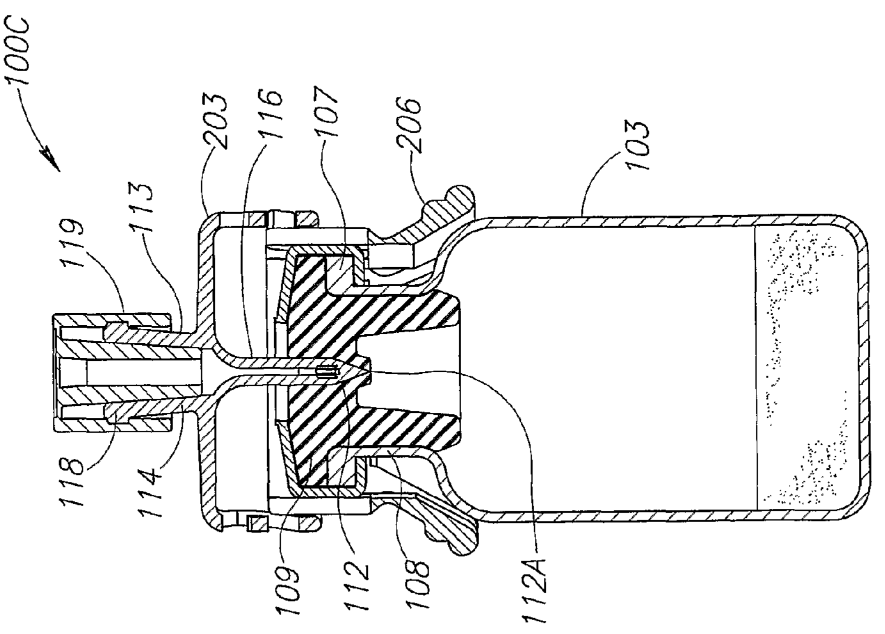
FIG. 15 is a longitudinal cross section of FIG. 14's vial assemblage along line C-C in FIG. 14.
Figure 14:
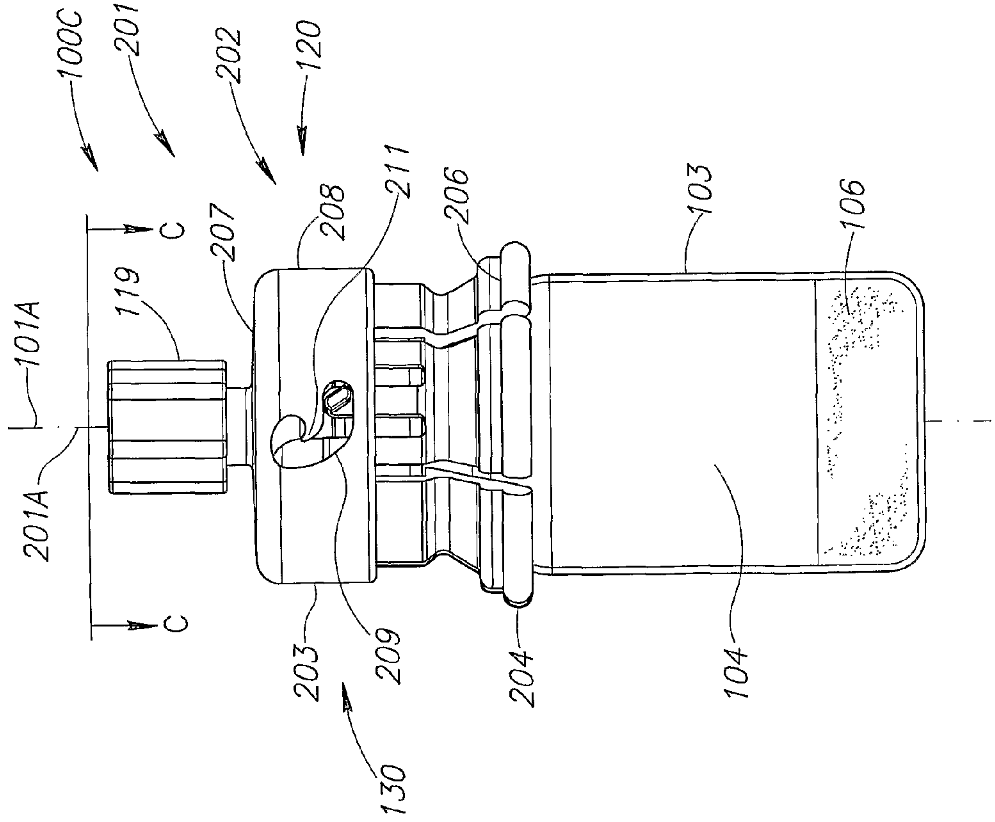
FIG. 14 is a front elevation view of an upright vial assemblage including a vial and a third preferred embodiment of a pre-attached fluid transfer device having a depress and twist safety catch mechanism in an initial set-up position.
Figure 16:
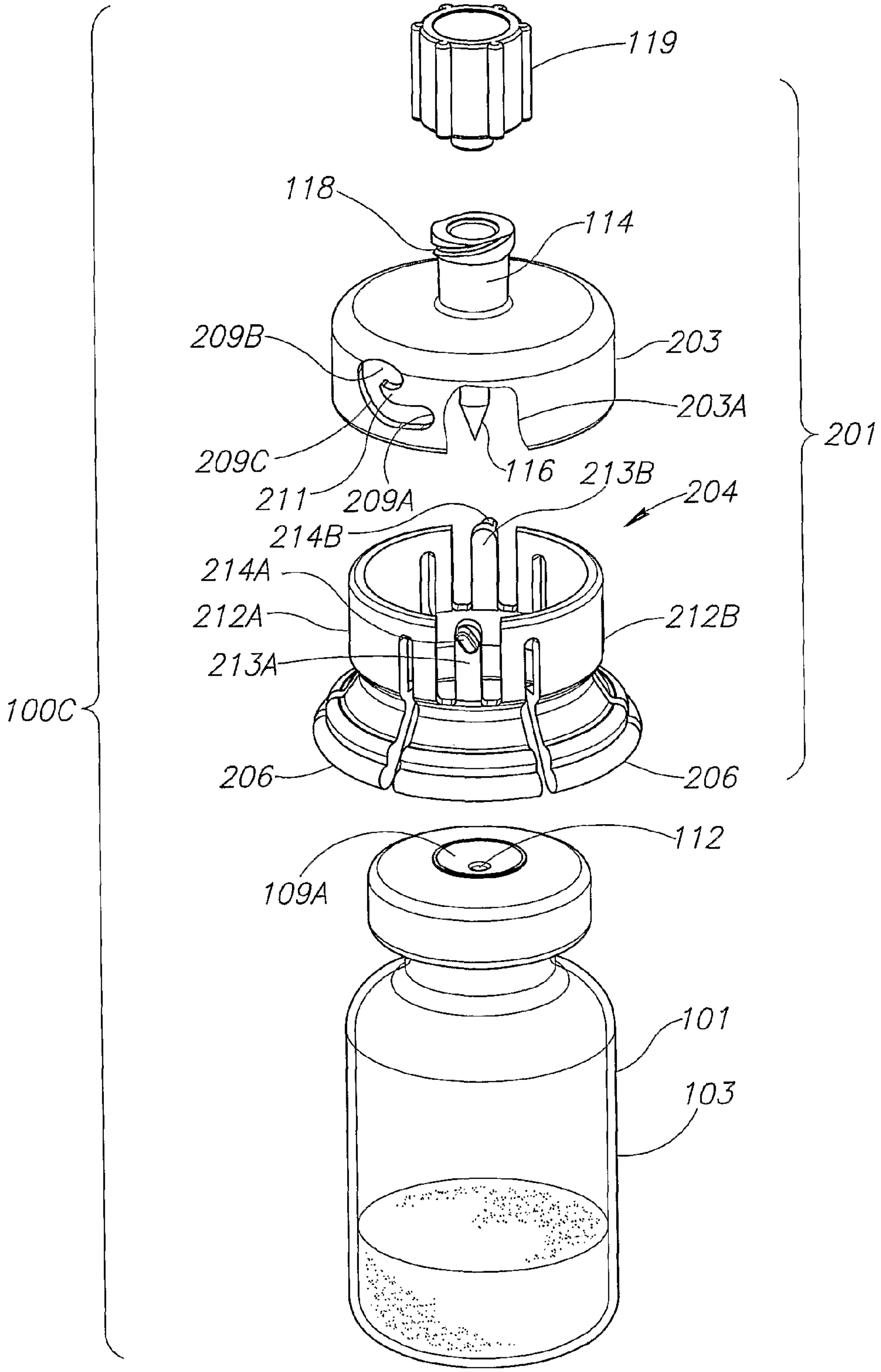
FIG. 16 is an exploded view of FIG. 14's vial assemblage.
Figure 18:
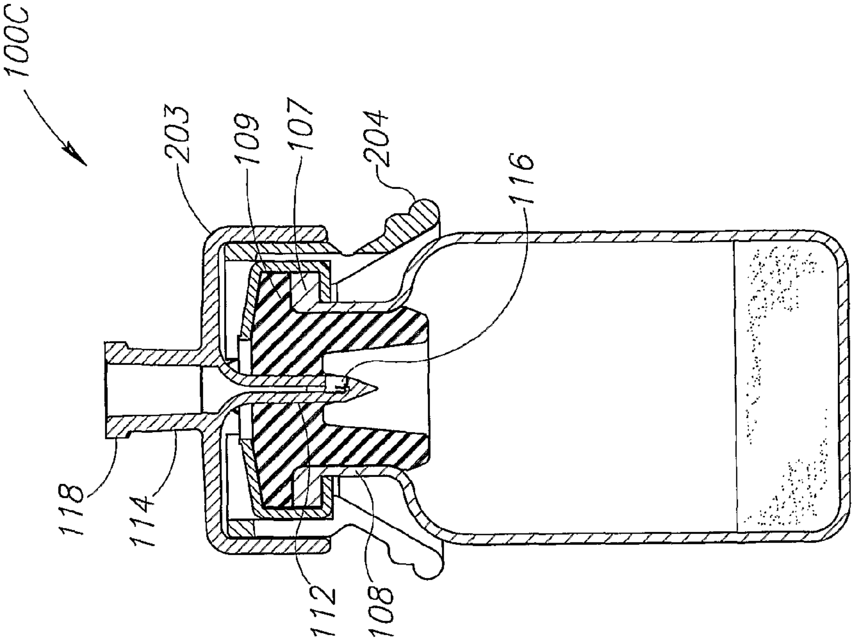
FIG. 18 is a longitudinal cross section of FIG. 17's vial assemblage along line C-C in FIG. 17.

FIGS. 14 to 16 show a vial assemblage 100C including a vial 101 and a fluid transfer device 201 having a longitudinal axis 201A substantially coaxial with the vial's longitudinal axis 101A. The fluid transfer device 201 includes an elongated tubular flow member 113 with a connector 114 with an external screw thread 118, a spike 116 with a spike end 116A, a lumen 117 and a screw cap 119. The fluid transfer device 201 includes a flow member arrest arrangement 120 for stopping displacement of the flow member 113 toward the vial 101 on manual urging of the flow member 113 from its non-flow communication set-up position to its flow communication position. The fluid transfer device 201 includes a flow member securing arrangement 130 for preventing upward displacement of the flow member 113 on manual removal of the closure 119 from the connector 114.

The fluid transfer device 201 includes a twist and depress safety catch mechanism 202 for preventing inadvertent downward displacement of the flow member 113 from an initial non-flow communication set-up position to a subsequent flow communication position for urging the spike end 116A through the stopper 109 into the vial interior 104. The safety catch mechanism 202 includes a cap-like member 203 integrally formed on the flow member 113 and telescopically mounted on a vial gripping member 204 having downward depending spaced apart flex members 206 for telescopically snap fitting onto the vial rim 107. FIG. 16 show the cap-like member 203 with a cut-away 203A to show the spike 116 which would otherwise be obscured from view. The fluid transfer device 201 further includes a tamper-proof arrangement 160 for preventing a user returning the safety catch mechanism 202 to its initial position once a user has primed same ready for manually urging the flow member 113 from its initial set-up position to its subsequent flow communication position.

Figure 17:
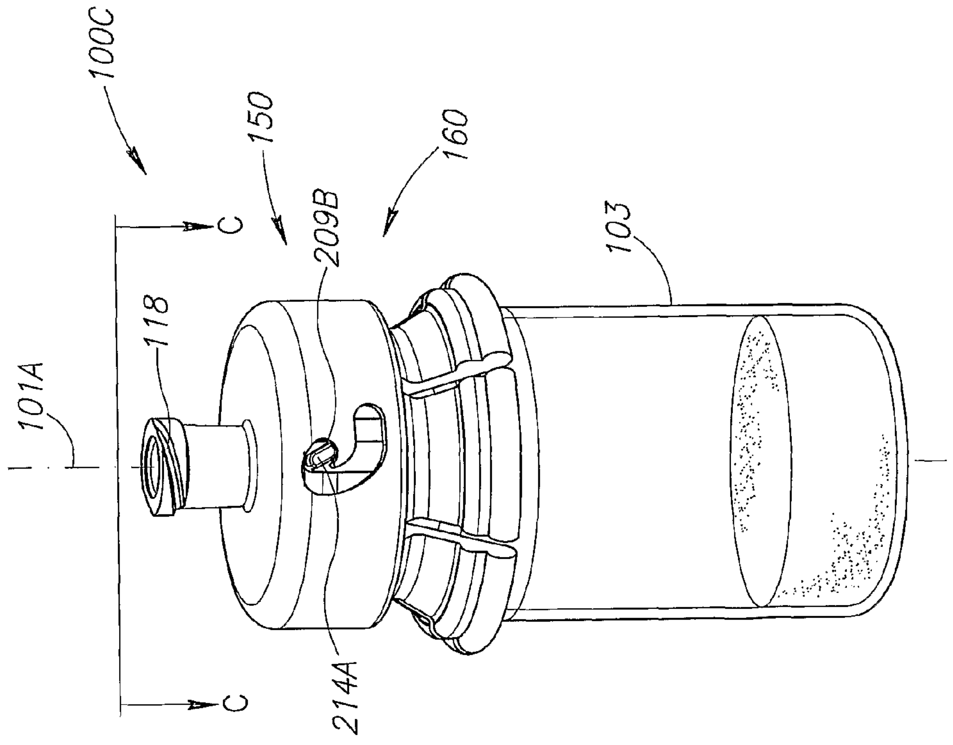
FIG. 17 is a front isometric view of FIG. 14's vial assemblage in a subsequent flow communication position.

The cap-like member 203 includes a top wall 207, and a downward depending skirt 208 formed with a pair of diametrically opposite slots 209 each having a generally U-shaped configuration disposed sideways with its open end facing in a counterclockwise direction. FIGS. 14, 16 and 17 show the front slot 209 only. The U-shaped slots 209 each include a substantially horizontal lowermost section 209A, a substantially horizontal uppermost section 209B and an upwardly inclined section 209C extending between the sections 209A and 209B. The skirt 208 is formed with a pair of latch members 211 at the junctions between the uppermost sections 209B and the inclined sections 209C for acting as part of the flow member securing arrangement 130 and the tamper-proof arrangement 160.

The vial gripping member 204 includes opposite side walls 212A and 212B and opposite upright resiliently flexible safety catches 213A and 213B interposed between the opposite side walls 212A and 212B. The safety catches 213 each have a radial outward pin 214 for traveling along their corresponding U-shaped slots 209. The safety catches 213 are intentionally capable of being flexed clockwise and counterclockwise relative to their unflexed upright positions. The pins 214 remain latched in the uppermost sections 209B by virtue of the latch members 211 thereby facilitating the counterclockwise unscrewing of the screw cap 119 as the pins 214 bear against the latch members 211. The pins 214 remain latched in the uppermost sections 209B on clockwise screwing of a syringe 140 onto the connector 114 as the pins 214 bear against the free ends of the uppermost sections 209B.

The safety catch mechanism 202, the flow member arrest arrangement 120, the flow member securing arrangement 130 and the tamper-proof arrangement 160 are operative with a single slot 209 and a safety catch 213. Provision of dual safety catches 213 ensures a more robust arrangement.

Figure 19:
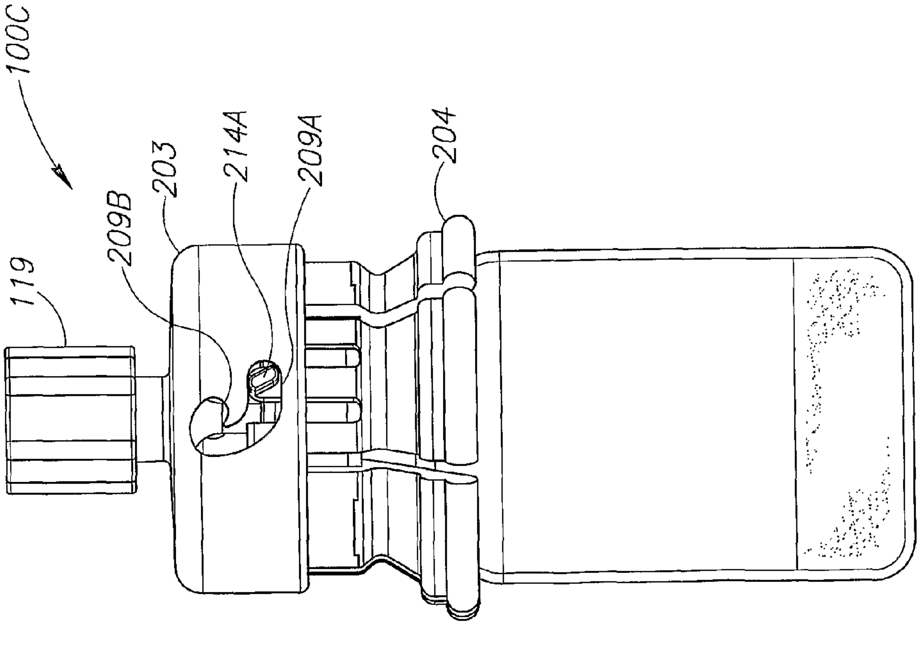

FIGS. 19 to 23 show the use of the vial assemblage 100C as follows:

FIG. 19 shows the vial assemblage 100C in its set-up position in which the cap-like member 203 is raised with respect to the vial gripping member 204, the safety catches 213 are in their upright positions and their pins 214 are located at the free ends of their lower sections 209As, the spike end 116A is pre-inserted in the stopper 109 proximate the bore end 112A, and the screw cap 119 seals the connector 114.

Figure 20:
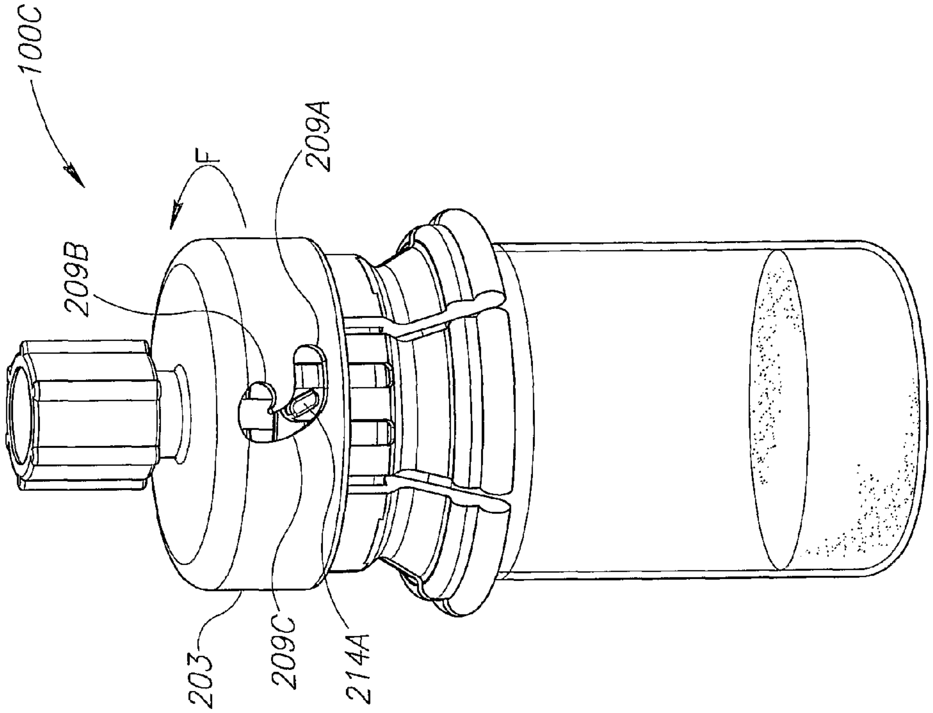
FIGS. 19 to 23 show the use of FIG. 14's vial assemblage.

FIG. 20 shows priming of the vial assemblage 100C ready for use by manually rotating the cap-like member 203 in a clockwise direction depicted by arrow F relative to the vial gripping member 204 whereby the pins 214 are located at the junctures between the lower sections 209A and the upright sections 209C.

Figure 21:
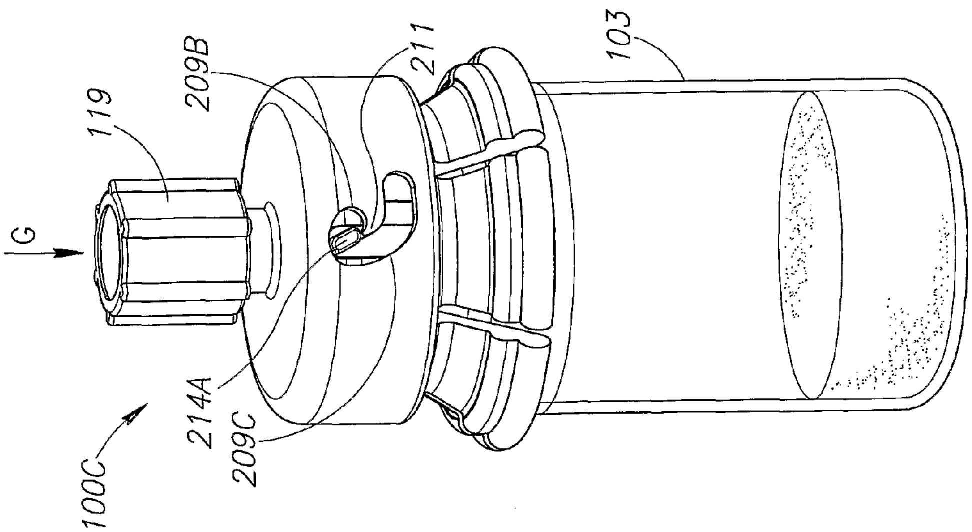

FIG. 21 shows the vial assemblage 100C in its flow communication position subsequent to depression of the cap-like Member 203 towards the vial gripping member 204 as depicted by arrow G to puncture the stopper 109. The safety catches 213 are initially flexed in a counterclockwise direction as the pins 214 are forcibly urged along the upright section 209C on depression of the cap-like member 203. The safety catches 213 are able to revert to their unflexed positions by urging their pins 214 to snap past the latch members 211 thereby preventing a user to return the cap-like member 203 to its initial position (see FIG. 19).

Figure 22:
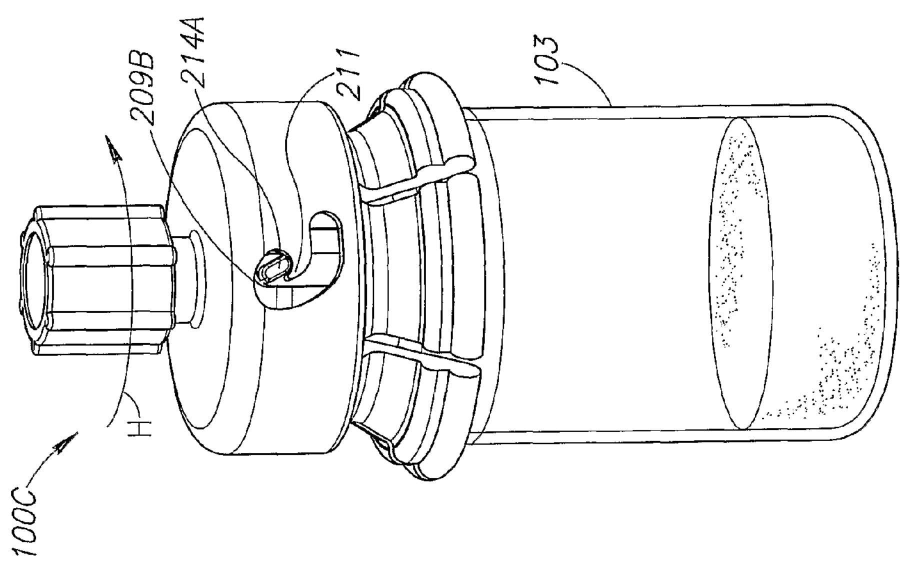

FIG. 22 shows the counterclockwise unscrewing of the screw cap 119 as denoted by arrow H to expose the connector 114.

Figure 23:
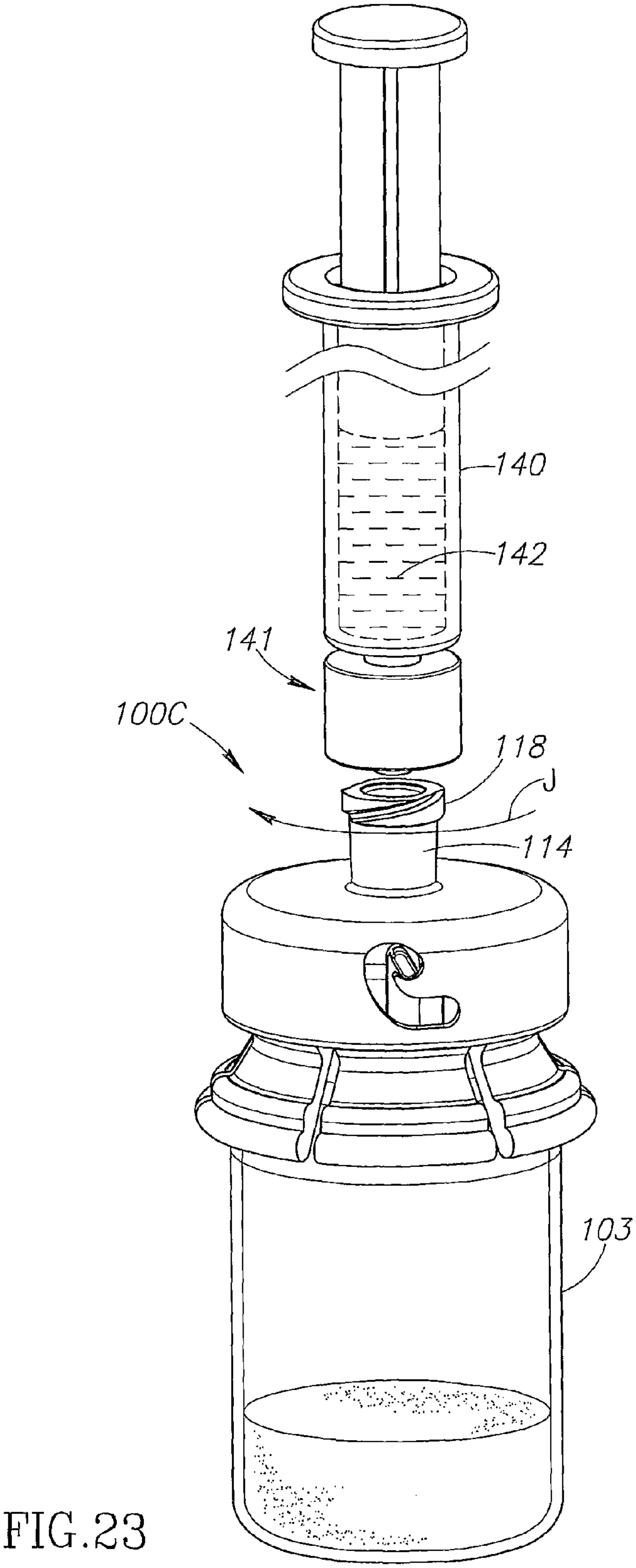

FIG. 23 shows the clockwise screwing of a needleless syringe 140 in a clockwise direction J onto the connector 114 for enabling flow communication between the syringe 140 and the vial interior 104.

While the invention has been described with respect to a limited number of embodiments, it will be appreciated that many variations, modifications, and other applications of the invention can be made within the scope of the appended claims.

The invention claimed is:

1. A vial assemblage for use with a needleless syringe, the assemblage comprising:

(a) a vial having a longitudinal axis and including a vial body having a vial interior for storing a medicament, a vial rim defining a vial opening, and a stopper for sealing said vial, said stopper having an uppermost stopper surface and a pre-formed axial blind bore with a bore end of reduced stopper thickness between said blind bore and said vial interior; and (b) a fluid transfer device having a longitudinal axis for substantial co-axial alignment with said longitudinal axis of said vial and including:

i) an elongated tubular flow member having a connector for sealing flow communication with the needleless syringe and a spike having a spike end for puncturing said stopper for enabling flow communication between the needleless syringe and said vial interior, said flow member being manually urged from an initial non-flow communication set-up position with said spike end disposed in said stopper to a subsequent flow communication position with said spike end puncturing said bore end for protruding a predetermined distance into said vial interior for flow communication purposes, said spike end being in intimate sealing contact with said stopper in said non-flow communication set-up position and protruding beyond said bore end into said vial interior in said flow communication position, and ii) a manually removable closure for initially sealing said connector in said non-flow communication set-up position and, on removal, exposing said connector in said flow communication position for enabling sealing connection with the needleless syringe.

2. The assemblage according to claim 1 wherein said connector has an external screw thread and said closure is constituted by a screw cap screw threaded on said external screw thread, whereby said flow member securing arrangement prevents rotation of said flow member relative to said stopper during unscrewing of said screw cap from said screw thread.

3. The assemblage according to claim 1, wherein said fluid transfer device includes a flow member arrest arrangement for stopping displacement of said flow member at said predetermined distance in said flow communication position.

4. The assemblage according to claim 2 wherein said flow member arrest arrangement includes a flange intermediate said connector and said spike, wherein said flange is disposed above said uppermost stopper surface in said non-flow communication set-up position and bears against said uppermost stopper surface in said flow communication position.

5. The assemblage according to claim 1 wherein said fluid transfer device includes a flow member securing arrangement for preventing upward displacement of said flow member on manual removal of said closure from said connector.

6. The assemblage according to claim 5 wherein said flow member securing arrangement includes at least one barb along said flow member disposed above said uppermost stopper surface in said non-flow communication set-up position and in said stopper in said flow communication position.

7. The assemblage according to claim 1 wherein said fluid transfer device further includes a safety catch mechanism for preventing inadvertent displacement of said flow member from said non-flow communication set-up position to said flow communication position.

8. The assemblage according to claim 7 wherein said fluid transfer device further includes a tamper-proof arrangement for preventing a user returning said safety catch mechanism to an initial position once a user has primed same ready for manually urging said flow member from said non-flow communication set-up position to said flow communication position.

9. The assemblage according to claim 7 wherein said vial includes a vial neck intermediate said vial rim and said vial body, said flow member arrest arrangement includes a flange intermediate said connector and said spike wherein said flange is disposed above said uppermost stopper surface in said non-flow communication set-up position, and said safety catch mechanism includes a removable safety catch having an upper flange grip for gripping said flange, a lower neck grip for gripping said vial neck and an upright rod extending between said upper flange grip and said lower neck grip.

10. The assemblage according to claim 7 wherein said safety catch mechanism includes a safety pull ring for detaching said removable safety catch from said vial, said safety pull ring having an initial downward position co-directional with said longitudinal axis of said vial and is manually urged upwardly into a subsequent transverse position relative to said longitudinal axis of said vial for enabling removal of said safety catch.

11. The assemblage according to claim 10 including a detent for precluding returning said safety pull ring from said subsequent transverse position to said initial downward position.

12. The assemblage according to claim 7 wherein said safety catch mechanism includes a vial gripping member having downward depending spaced apart flex members for telescopically snapping fitting onto said vial rim and a cap-like member integrally formed with said flow member and telescopically mounted on said vial gripping member for being manually urged from said non-flow communication set-up position to said flow communication position for urging said spike end through said stopper into said vial interior.

13. The assemblage according to claim 12 wherein said vial gripping member includes at least one upright resiliently flexible catch member with a radial outward pin and said cap-like member includes at least one slot wherein said at least one radial outward pin travels along a corresponding said slot for enabling said cap-like member to be telescopically mounted on said vial gripping member.

14. The assemblage according to claim 13 wherein each slot has a generally U-shaped configuration with an open end facing in a counterclockwise direction in an upright position of said vial assemblage thereby acting as said flow member securing arrangement.

15. The assemblage according to claim 14 wherein each slot includes a substantially horizontal lowermost section, a substantially horizontal uppermost section and an upwardly inclined section extending between said substantially horizontal lowermost section and substantially horizontal uppermost section, and a latch member disposed at a juncture between said substantially horizontal uppermost section and said upwardly inclined section, whereby said radial outward pin snaps past said corresponding latch member in said flow communication for preventing a user returning said safety catch mechanism to an initial position once a user has primed said safety catch mechanism ready for manually urging said flow member from said initial set-up position to said subsequent flow communication position.

16. A vial for use in the vial assemblage according to claim 1.

17. A fluid transfer device for use in the vial assemblage according to claim 1.

* * * * *